(12) United States Patent
Baba-Ahmed et al.

(10) Patent No.: US 10,435,341 B2
(45) Date of Patent: Oct. 8, 2019

(54) METHOD FOR PRODUCING AND PURIFYING 2,3,3,3-TETRAFLUORO-1-PROPENE

(71) Applicant: Arkema France, Colombes (FR)

(72) Inventors: Abdelatif Baba-Ahmed, Saint-fons (FR); Bertrand Collier, Saint-genis-laval (FR); Dominique Deur-Bert, Charly (FR); Irène Emery, Francheville (FR); Laurent Wendlinger, Soucieu en Jarrest (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 16/063,301

(22) PCT Filed: Dec. 14, 2016

(86) PCT No.: PCT/EP2016/080952
§ 371 (c)(1),
(2) Date: Jun. 18, 2018

(87) PCT Pub. No.: WO2017/108524
PCT Pub. Date: Jun. 29, 2017

(65) Prior Publication Data
US 2018/0370880 A1 Dec. 27, 2018

(30) Foreign Application Priority Data
Dec. 23, 2015 (FR) .................... 15 63169

(51) Int. Cl.
*C07C 17/386* (2006.01)
*C07C 21/18* (2006.01)
*C07C 19/08* (2006.01)
*C07C 17/25* (2006.01)
*C09K 5/04* (2006.01)

(52) U.S. Cl.
CPC ............ *C07C 17/386* (2013.01); *C07C 17/25* (2013.01); *C07C 19/08* (2013.01); *C07C 21/18* (2013.01); *C09K 5/045* (2013.01); *C09K 2205/126* (2013.01)

(58) Field of Classification Search
CPC .................................................. C07C 17/386
See application file for complete search history.

(56) References Cited

U.S. PATENT DOCUMENTS

2013/0105296 A1* 5/2013 Chaki ..................... C01B 7/196
203/60
2017/0320798 A1* 11/2017 Shimokawa .......... C07C 17/386

FOREIGN PATENT DOCUMENTS

WO 2012011609 A1 1/2012

OTHER PUBLICATIONS

EPO, International Search Report in International Patent Application No. PCT/EP2016/080952 dated Feb. 9, 2017.

* cited by examiner

*Primary Examiner* — Medhanit W Bahta
(74) *Attorney, Agent, or Firm* — NK Patent Law

(57) ABSTRACT

The invention relates to a method for purifying 2,3,3,3-tetrafluoro-1-propene (1234yf) using a first composition comprising 2,3,3,3-tetrafluoro-1-propene, 1,1,1,2,2-pentafluoropropane (245cb) and trans-1,3,3,3-tetrafluoro-1-propene (1234ze-E), said method comprising the steps of: (a) bringing said first composition into contact with at least one organic extraction agent in order to form a second composition; (b) extractive distillation of said second composition in order to form a third composition comprising said organic extraction agent and trans-1,3,3,3-tetrafluoro-1-propene (1234ze-E), and a stream comprising the 2,3,3,3-tetrafluoro-1-propene and the 1,1,1,2,2-pentafluoropropane (245cb); and (c) recovery and separation of said third composition in order to form a stream comprising said organic extraction agent and a stream comprising the trans-1,3,3,3-tetrafluoro-1-propene (1234ze-E). The invention also relates to a method for producing 2,3,3,3-tetrafluoro-1-propene.

14 Claims, 4 Drawing Sheets

METHOD FOR PRODUCING AND PURIFYING 2,3,3,3-TETRAFLUORO-1-PROPENE

CROSS REFERENCE TO RELATED APPLICATIONS

This application is a U.S. National Stage application of International Application No. PCT/EP2016/080952 filed on Dec. 14, 2016, which claims the benefit of French Patent Application No. 1563169 filed on Dec. 23, 2015, the entire content of all of which is incorporated by reference herein.

TECHNICAL FIELD OF THE INVENTION

The invention relates to a process for purifying 2,3,3,3-tetrafluoro-1-propene. The invention also relates to a process for producing and purifying 2,3,3,3-tetrafluoro-1-propene.

TECHNOLOGICAL BACKGROUND OF THE INVENTION

Hydrofluorocarbons (HFCs) and in particular hydrofluoroolefins (HFOs), such as 2,3,3,3-tetrafluoro-1-propene (HFO-1234yf), are compounds known for their properties as coolants, heat-transfer fluids, extinguishers, propellants, foaming agents, swelling agents, gaseous dielectrics, polymerization medium or monomer, support fluids, agents for abrasives, drying agents and fluids for power production units. HFOs have been identified as desirable alternatives to HCFC on account of their low ODP (ozone depletion potential) and GWP (global warming potential) values.

Most of the processes for manufacturing hydrofluoroolefins involve a fluorination and/or dehydrohalogenation reaction. This type of reaction is performed in the gas phase and generates impurities which consequently need to be removed in order to obtain the desired compound in a sufficient degree of purity for the targeted applications.

For example, in the context of producing 2,3,3,3-tetrafluoro-1-propene (HFO-1234yf), the presence of impurities such as trans-1,3,3,3-tetrafluoro-1-propene (1234ze-E) is observed. Side products, for instance 1,1,1,2,2-pentafluoropropane, are also formed. Purification of this type of reaction mixture may be performed, for example, by distillation. However, when the compounds to be purified have boiling points that are too close or when they form azeotropic or quasi-azeotropic compositions, distillation is not an efficient process. Extractive distillation processes have thus been described.

WO 03/068716 discloses a process for recovering pentafluoroethane from a mixture comprising pentafluoroethane and chloropentafluoroethane by distillation in the presence of hexafluoropropene.

WO 98/19982 also discloses a process for purifying 1,1-difluoroethane by extractive distillation. The process consists in placing an extracting agent in contact with a mixture of 1,1-difluoroethane and vinyl chloride. The extracting agent is chosen from hydrocarbons, alcohols and chlorocarbons with a boiling point of between 10° C. and 120° C. As mentioned by WO 98/19982, the selection of the extracting agent may prove to be complex depending on the products to be separated.

SUMMARY OF THE INVENTION

The present invention allows the purification of 2,3,3,3-tetrafluoro-1-propene. The present invention in particular allows the production of a stream comprising 2,3,3,3-tetrafluoro-1-propene and 1,1,1,2,2-pentafluoropropane with a low content of trans-1,3,3,3-tetrafluoro-1-propene (1234ze-E). The present invention thus allows the production of 2,3,3,3-tetrafluoro-1-propene in improved purity.

According to a first aspect, the present invention provides a process for purifying 2,3,3,3-tetrafluoro-1-propene (1234yf) using a first composition comprising 2,3,3,3-tetrafluoro-1-propene, 1,1,1,2,2-pentafluoropropane (245cb) and trans-1,3,3,3-tetrafluoro-1-propene (1234ze-E), said process comprising the steps of:
   a) placing said first composition in contact with at least one organic extracting agent to form a second composition;
   b) extractive distillation of said second composition to form:
      i) a third composition comprising said organic extracting agent and trans-1,3,3,3-tetrafluoro-1-propene (1234ze-E); and
      ii) a stream comprising 2,3,3,3-tetrafluoro-1-propene and 1,1,1,2,2-pentafluoropropane (245cb);
   c) recovery and separation of said third composition to form a stream comprising said organic extracting agent and a stream comprising trans-1,3,3,3-tetrafluoro-1-propene (1234ze-E).

Preferably, the separation of step c) is performed by distillation. Preferably, the stream comprising said organic extracting agent is recycled into step a). Preferably, the stream comprising trans-1,3,3,3-tetrafluoro-1-propene is purified or destroyed by incineration.

Preferably, the stream ii) comprising 2,3,3,3-tetrafluoro-1-propene and 1,1,1,2,2-pentafluoropropane (245cb) formed in step b) is recovered. The stream may be purified to separate out 2,3,3,3-tetrafluoro-1-propene and 1,1,1,2,2-pentafluoropropane (245cb). Thus, according to a preferred embodiment, the process also comprises a step of recovering said stream comprising 2,3,3,3-tetrafluoro-1-propene and 1,1,1,2,2-pentafluoropropane (245cb) obtained in step b), and of distilling said stream to form a stream A comprising 2,3,3,3-tetrafluoro-1-propene and a stream B comprising 1,1,1,2,2-pentafluoropropane (245cb). Stream B comprising 1,1,1,2,2-pentafluoropropane (245cb) may be recycled into step A) of the process for producing and purifying 2,3,3,3-tetrafluoro-1-propene described above. Stream A comprising 2,3,3,3-tetrafluoro-1-propene may be purified to reach a degree of purity that meets the commercial specifications, i.e. free of or containing only a small content of 1,1,1,2,2-pentafluoropropane or of trans-1,3,3,3-tetrafluoro-1-propene.

According to a preferred embodiment, said first composition also comprises at least one of the compounds chosen from the group consisting of chloromethane (40), 1,1-difluoroethane (152a), 1,1,1,2-tetrafluoroethane (134a), chloropentafluoroethane (115), trans-1,2,3,3,3-pentafluoropropene (1225ye-E), cis-1,2,3,3,3-pentafluoropropene (1225ye-Z) and 3,3,3-trifluoropropene (1243zf).

According to a preferred embodiment, said at least one of the compounds chosen from the group consisting of chloromethane (40), 1,1-difluoroethane (152a), 1,1,1,2-tetrafluoroethane (134a), chloropentafluoroethane (115), trans-1,2,3,3,3-pentafluoropropene (1225ye-E), cis-1,2,3,3,3-pentafluoropropene (1225ye-Z) and 3,3,3-trifluoropropene (1243zf) are also contained in said second and third compositions; step c) of the present process being the recovery and separation of said third composition between, on the one hand, a stream comprising said organic extracting agent and, on the other hand, a stream comprising trans-1,3,3,3-tetrafluoro-1-propene (1234ze-E) and said at least one of the compounds chosen from the group consisting of chloromethane (40), 1,1-difluoroethane (152a), 1,1,1,2-tetrafluoroethane (134a), chloropentafluoroethane (115), trans-1,2,3,3,3-pentafluoropropene (1225ye-E), cis-1,2,3,3,3-pentafluoropropene (1225ye-Z) and 3,3,3-trifluoropropene (1243zf).

Preferably, said organic extracting agent may have a boiling point of between 10 and 150° C.

According to a preferred embodiment, said organic extracting agent is a solvent chosen from the group consisting of halohydrocarbon, alcohol, ketone, amine, ester, ether, aldehyde, nitrile, carbonate, thioalkyl, amide and heterocycle; or the organic extracting agent is triethylfluorosilane. Preferably, the organic extracting agent is chosen from the group consisting of amine, ether, ester, aldehyde, ketone, alcohol and heterocycle.

According to a preferred embodiment, said organic extracting agent has a separation factor $S_{1,2}$ of greater than or equal to 1.1, said separation factor being calculated by the formula $S_{1,2}=(\gamma_{1,S}*P1)/(\gamma_{2,S}*P2)$ in which
$\gamma_{1,S}$ represents the activity coefficient of 2,3,3,3-tetrafluoro-1-propene in said organic extracting agent at infinite dilution;
P1 represents the saturating vapor pressure of 2,3,3,3-tetrafluoro-1-propene;
$\gamma_{2,S}$ represents the activity coefficient of trans-1,3,3,3-tetrafluoro-1-propene (1234ze-E) in said organic extracting agent at infinite dilution;
P2 represents the saturating vapor pressure of trans-1,3,3,3-tetrafluoro-1-propene (1234ze-E);
advantageously, the separation factor is greater than or equal to 1.2, preferably greater than or equal to 1.4, more preferentially greater than or equal to 1.6, in particular greater than or equal to 1.8.

According to a preferred embodiment, said organic extracting agent has an absorption capacity $C_{2,S}$ of greater than or equal to 0.20, said absorption capacity being calculated by the formula $C_{2,S}=1/(\gamma_{2,S})$ in which $\gamma_{2,S}$ represents the activity coefficient of said at least one compound consisting of trans-1,3,3,3-tetrafluoro-1-propene (1234ze-E) in said organic extracting agent at infinite dilution; preferably, $\gamma_{2,S}$ represents the activity coefficient of said at least one compound consisting of trans-1,3,3,3-tetrafluoro-1-propene (1234ze-E), in said organic extracting agent at infinite dilution;
advantageously, the absorption capacity $C_{2,S}$ is greater than or equal to 0.40, preferably greater than or equal to 0.60, more preferentially greater than or equal to 0.80, in particular greater than or equal to 1.0.

According to a preferred embodiment, said organic extracting agent may also have a separation factor $S_{1,2}$ of greater than or equal to 1.1, said separation factor being calculated by the formula $S_{1,2}=(\gamma_{1,S}*P1)/(\gamma_{2,S}*P2)$ in which
$\gamma_{1,S}$ represents the activity coefficient of 1,1,1,2,2-pentafluoropropane (245cb) in said organic extracting agent at infinite dilution;
P1 represents the saturating vapor pressure of 1,1,1,2,2-pentafluoropropane (245cb);
$\gamma_{2,S}$ represents the activity coefficient of trans-1,3,3,3-tetrafluoro-1-propene (1234ze-E) in said organic extracting agent at infinite dilution;
P2 represents the saturating vapor pressure of trans-1,3,3,3-tetrafluoro-1-propene (1234ze-E);
advantageously, the separation factor is greater than or equal to 1.2, preferably greater than or equal to 1.4, more preferentially greater than or equal to 1.6, in particular greater than or equal to 1.8, more particularly greater than or equal to 2.0.

According to a preferred embodiment, said first composition may comprise 2,3,3,3-tetrafluoro-1-propene, 1,1,1,2,2-pentafluoropropane (245cb), trans-1,3,3,3-tetrafluoro-1-propene (1234ze-E) and optionally or not at least one of the compounds chosen from the group consisting of chloromethane (40), 1,1-difluoroethane (152a), 1,1,1,2-tetrafluoroethane (134a), chloropentafluoroethane (115), trans-1,2,3,3,3-pentafluoropropene (1225ye-E), cis-1,2,3,3,3-pentafluoropropene (1225ye-Z) and 3,3,3-trifluoropropene (1243zf).

According to a preferred embodiment, said organic extracting agent is chosen from the group consisting of ethylamine, isopropylamine, diethyl ether, n-propylamine, diethylamine, propanone, methyl acetate, butanone, diethoxymethane, isopropyl acetate, 3-pentylamine, 2-methoxyethanamine, tert-butyl acetate, dioxane, 1,1-diethoxyethane, trimethoxymethane, n-pentylamine, 1,3-dioxane, sec-butyl acetate, 1,2-diaminoethane, 1-methoxy-2-propanol, 1,2-propanediamine, n-butyl acetate, 2-methoxy-1-propanol and hexanal. Preferably, said organic extracting agent is chosen from the group consisting of ethylamine, isopropylamine, diethyl ether, n-propylamine, diethylamine, diethoxymethane, isopropyl acetate, 3-pentylamine, 2-methoxyethanamine, tert-butyl acetate, dioxane, 1,1-diethoxyethane, trimethoxymethane, n-pentylamine, 1,3-dioxane, sec-butyl acetate, 1,2-diaminoethane, 1-methoxy-2-propanol, 1,2-propanediamine, n-butyl acetate, 2-methoxy-1-propanol and hexanal.

According to a preferred embodiment, the stream comprising 2,3,3,3-tetrafluoro-1-propene and 1,1,1,2,2-pentafluoropropane (245cb) formed in step b) is recovered and is free of trans-1,3,3,3-tetrafluoro-1-propene (1234ze-E).

According to a preferred embodiment, said process comprises, prior to step a), the following steps:
i') use of a composition comprising 2,3,3,3-tetrafluoro-1-propene, impurities with a boiling point below the boiling point of 2,3,3,3-tetrafluoro-1-propene, 1,1,1,2,2-pentafluoropropane (245cb), and trans-1,3,3,3-tetrafluoro-1-propene (1234ze-E), optionally or not at least one compound chosen from the group consisting of chloromethane (40), 1,1-difluoroethane (152a), 1,1,1,2-tetrafluoroethane (134a), chloropentafluoroethane (115), trans-1,2,3,3,3-pentafluoropropene (1225ye-E), cis-1,2,3,3,3-pentafluoropropene (1225ye-Z), 3,3,3-trifluoropropene (1243zf), and optionally or not heavy impurities;
ii') distillation of said composition from step i) to remove, at the top of the column, impurities with a boiling point below the boiling point of 2,3,3,3-tetrafluoro-1-propene and to form a first stream comprising 2,3,3,3-tetrafluoro-1-propene, 1,1,1,2,2-pentafluoropropane (245cb) and trans-1,3,3,3-tetrafluoro-1-propene (1234ze-E), optionally or not at least one compound chosen from the group consisting of chloromethane (40), 1,1-difluoroethane (152a), 1,1,1,2-tetrafluoroethane (134a), chloropentafluoroethane (115), trans-1,2,3,3,3-pentafluoropropene (1225ye-E), cis-1,2,3,3,3-pentafluoropropene (1225ye-Z), 3,3,3-trifluoropropene (1243zf), and optionally or not heavy impurities, recovered at the bottom of the distillation column;
iii') optionally or not, distillation of said first stream recovered at the bottom of the distillation column in step ii') to recover, at the top of the column, a second stream comprising 2,3,3,3-tetrafluoro-1-propene, 1,1,1,2,2-pentafluoropropane (245cb) and trans-1,3,3,3-tetrafluoro-1-propene (1234ze-E), and optionally or not at least one compound chosen from the group consisting of chloromethane (40), 1,1-difluoroethane (152a), 1,1,1,2-tetrafluoroethane (134a), chloropentafluoroethane (115), trans-1,2,3,3,3-pentafluoropropene (1225ye-E), cis-1,2,3,3,3-pentafluoropropene (1225ye-Z) and 3,3,3-trifluoropropene (1243zf), and, at the bottom of the distillation column, a stream comprising the heavy impurities;

said at first stream recovered in step ii') or said second stream recovered in step iii') corresponding to said first composition used in step a).

The heavy impurities may contain, for example, 1,1,1,3,3,3-hexafluoropropane (236fa), 1,1,1,2,3,3-hexafluoropropane (236ea), 1,1,1,2,3,3,3-heptafluoropropane (227ca), cis-1,3,3,3-tetrafluoro-1-propene (1234ze-Z), and dimers or trimers derived from one of the compounds present in the composition or the stream under consideration.

According to a second aspect, the invention provides a process for producing and purifying 2,3,3,3-tetrafluoro-1-propene, comprising the steps of:
  A) fluorination in the presence of a catalyst, of a compound of formula $CX(Y)_2—CX(Y)_m—CH_mXY$ (I) in which X and Y independently represent H, F or Cl and m=0 or 1; and/or catalytic fluorination in the presence of a catalyst of a compound of formula $(CX_nY_{3-n})CH_pX_{1-p}CH_mX_{2-m}$ (II) in which X is, independently of each other, Cl, F, I or Br; Y is, independently of each other, H, Cl, F, I or Br; n is 1, 2 or 3; and m is 0, 1 or 2; and p is 0 or 1;
  B) recovery of a stream comprising 2,3,3,3-tetrafluoro-1-propene, 1,1,1,2,2-pentafluoropropane (245cb), trans-1,3,3,3-tetrafluoro-1-propene (1234ze-E) and optionally or not at least one of the compounds chosen from the group consisting of chloromethane (40), 1,1-difluoroethane (152a), 1,1,1,2-tetrafluoroethane (134a), chloropentafluoroethane (115), trans-1,2,3,3,3-pentafluoropropene (1225ye-E), cis-1,2,3,3,3-pentafluoropropene (1225ye-Z) and 3,3,3-trifluoropropene (1243zf);
  C) implementation of the process for purifying 2,3,3,3-tetrafluoro-1-propene according to the present invention using the stream recovered in step B).

According to another aspect, the present invention provides a composition comprising 2,3,3,3-tetrafluoropropene, 1,1,1,2,2-pentafluoropropane (245cb), trans-1,3,3,3-tetrafluoro-1-propene (1234ze-E) and an organic extracting agent with a separation factor $S_{1,2}$ of greater than or equal to 1.60, said separation factor being calculated by the formula $S_{1,2}=(\gamma_{1,S}*P1)/(\gamma_{2,S}*P2)$ in which $\gamma_{1,S}$ represents the activity coefficient of 2,3,3,3-tetrafluoropropene in said organic extracting agent at infinite dilution, P1 represents the saturating vapor pressure of 2,3,3,3-tetrafluoropropene, $\gamma_{2,S}$ represents the activity coefficient of trans-1,3,3,3-tetrafluoro-1-propene (1234ze-E) in said organic extracting agent at infinite dilution, P2 represents the saturating vapor pressure of trans-1,3,3,3-tetrafluoro-1-propene (1234ze-E); and said organic extracting agent with a separation factor $S_{1,2}$ of greater than or equal to 1.60, said separation factor being calculated by the formula $S_{1,2}=(\gamma_{1,S}*P1)/(\gamma_{2,S}*P2)$ in which $\gamma_{1,S}$ represents the activity coefficient of 1,1,1,2,2-pentafluoropropane (245cb) in said organic extracting agent at infinite dilution, P1 represents the saturating vapor pressure of 1,1,1,2,2-pentafluoropropane (245cb), $\gamma_{2,S}$ represents the activity coefficient of trans-1,3,3,3-tetrafluoro-1-propene (1234ze-E) in said organic extracting agent at infinite dilution, P2 represents the saturating vapor pressure of trans-1,3,3,3-tetrafluoro-1-propene (1234ze-E); preferably, said organic extracting agent has an absorption capacity $C_{2,S}$ of greater than or equal to 0.60, said absorption capacity being calculated by the formula $C_{2,S}=1/(\gamma_{2,S})$ in which $\gamma_{2,S}$ represents the activity coefficient of trans-1,3,3,3-tetrafluoro-1-propene (1234ze-E) in said organic extracting agent at infinite dilution. According to a preferred embodiment, said organic extracting agent is chosen from the group consisting of ethylamine, isopropylamine, diethyl ether, n-propylamine, diethylamine, propanone, methyl acetate, butanone, diethoxymethane, isopropyl acetate, 3-pentylamine, 2-methoxyethanamine, tert-butyl acetate, dioxane, 1,1-diethoxyethane, trimethoxymethane, n-pentylamine, 1,3-dioxane, sec-butyl acetate, 1,2-diaminoethane, 1-methoxy-2-propanol, 1,2-propanediamine, n-butyl acetate, 2-methoxy-1-propanol and hexanal. Preferably, said organic extracting agent is chosen from the group consisting of ethylamine, isopropylamine, diethyl ether, n-propylamine, diethylamine, diethoxymethane, isopropyl acetate, 3-pentylamine, 2-methoxyethanamine, tert-butyl acetate, dioxane, 1,1-diethoxyethane, trimethoxymethane, n-pentylamine, 1,3-dioxane, sec-butyl acetate, 1,2-diaminoethane, 1-methoxy-2-propanol, 1,2-propanediamine, n-butyl acetate, 2-methoxy-1-propanol and hexanal. Preferably, said composition according to this other aspect of the invention is free of HF.

DETAILED DESCRIPTION OF THE INVENTION

Figure 1A:
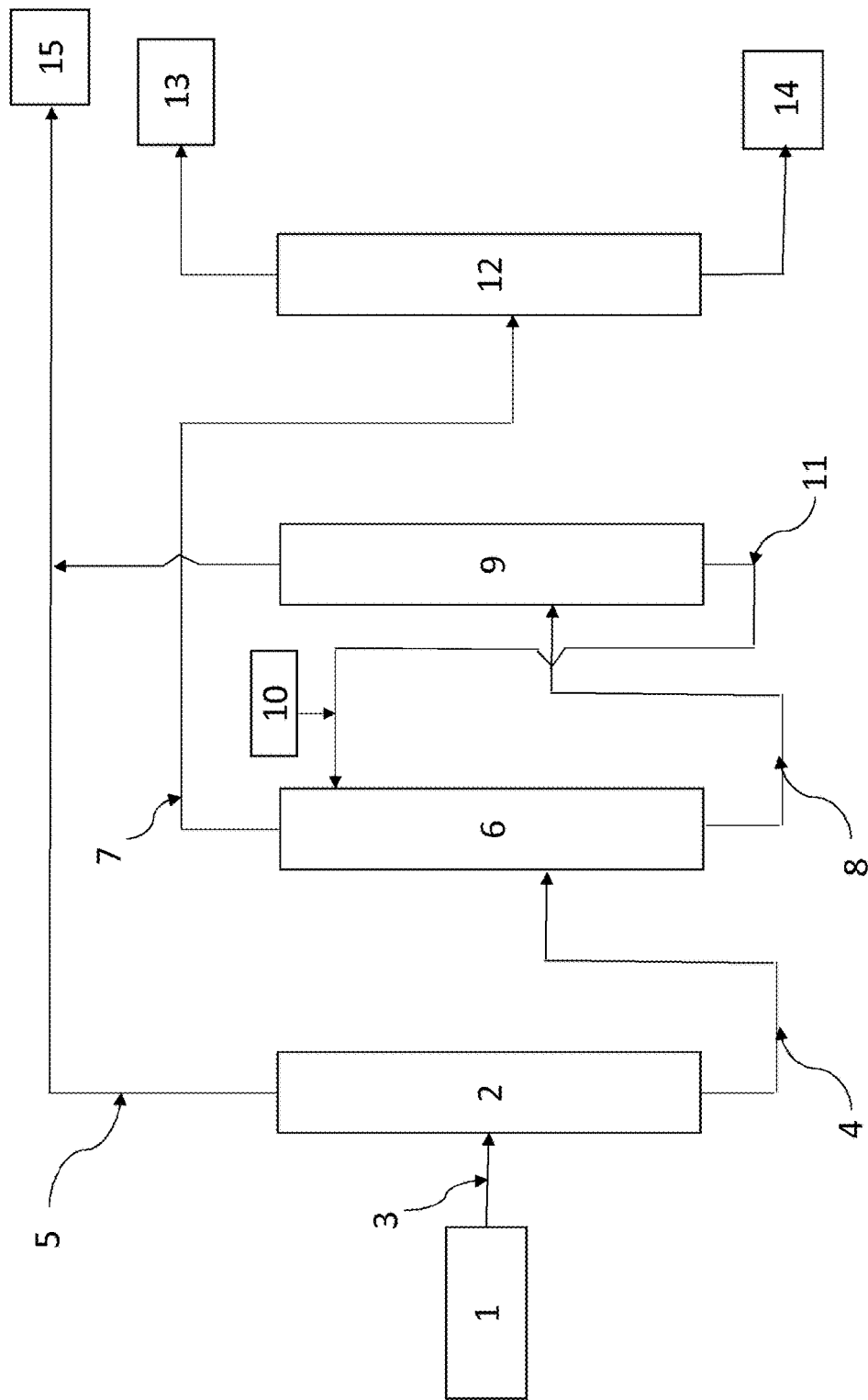
FIGS. 1a-c schematically represent a device for performing a process for purifying 2,3,3,3-tetrafluoro-1-propene according to a particular embodiment of the present invention.

The term "hydrocarbon" as used herein refers to linear or branched $C_1$-$C_{20}$ alkane, $C_3$-$C_{20}$ cycloalkane, $C_2$-$C_{20}$ alkene, $C_3$-$C_{20}$ cycloalkene or $C_6$-$C_{18}$ arene compounds. For example, the term "alkane" refers to compounds of formula $C_nH_{2n+2}$ in which n is between 1 and 20. The term "$C_1$-$C_{20}$ alkane" includes, for example, pentane, hexane, heptane, octane, nonane and decane, or isomers thereof. The term "$C_2$-$C_{20}$ alkene" refers to hydrocarbon-based compounds comprising one or more carbon-carbon double bonds and comprising from 2 to 20 carbon atoms. The term "$C_3$-$C_{20}$ cycloalkane" refers to a saturated hydrocarbon-based ring comprising from 3 to 20 carbon atoms. The term "$C_6$-$C_{18}$ aryl" refers to cyclic and aromatic hydrocarbon-based compounds comprising from 6 to 18 carbon atoms. The term "$C_3$-$C_{20}$ cycloalkene" refers to cyclic hydrocarbon-based compounds comprising from 3 to 20 carbon atoms and comprising one or more carbon-carbon double bonds.

The term "alkyl" denotes a monovalent radical derived from a linear or branched alkane, comprising from 1 to 20 carbon atoms. The term "cycloalkyl" denotes a monovalent radical derived from a cycloalkane, comprising from 3 to 20 carbon atoms. The term "aryl" denotes a monovalent radical derived from an arene, comprising from 6 to 18 carbon atoms. The term "alkenyl" denotes a monovalent radical of 2 to 20 carbon atoms and at least one carbon-carbon double bond. The term "alkynyl" denotes a monovalent radical of 2 to 20 carbon atoms and at least one carbon-carbon triple bond. The term "halogen" refers to an —F, —Cl, —Br or —I group. The term "cycloalkenyl" refers to a monovalent radical derived from a cycloalkene comprising from 3 to 20 carbon atoms. The $C_1$-$C_{20}$ alkyl, $C_2$-$C_{20}$ alkenyl, $C_2$-$C_{20}$ alkynyl, $C_3$-$C_{20}$ cycloalkyl, $C_3$-$C_{20}$ cycloalkenyl and $C_6$-$C_{18}$ aryl substituents may be optionally substituted with one or more —OH, halogen, —NR$^a$C(O)R$^b$, —C(O)NR$^a$R$^b$—CN, —NO$_2$, —NR$^a$R$^b$, —OR$^a$, —SR$^a$, —CO$_2$R$^a$, —OC(O)OR$^a$, —OC(O)R$^a$, —C(O)H or —C(O)R$^a$ substituents in which R$^a$ and R$^b$ are, independently of each other, hydrogen, unsubstituted $C_1$-$C_{20}$ alkyl, unsubstituted $C_2$-$C_{20}$ alkenyl, unsubstituted $C_2$-$C_{20}$ alkynyl, unsubstituted $C_3$-$C_{20}$ cycloalkyl, unsubstituted $C_3$-$C_{20}$ cycloalkenyl or unsubstituted $C_6$-$C_{18}$ aryl. In the substituents —NR$^a$R$^b$, —NR$^a$C(O)R$^b$, —C(O)NR$^a$R$^b$, R$^a$ and R$^b$ may form, with the nitrogen atom or with the functional group to which they are attached, a saturated or unsaturated, aromatic or non-aromatic, 4- to 10-membered heterocycle.

The term "halohydrocarbons" refers to compounds of formula R$^a$X in which R$^a$ is chosen from $C_1$-$C_{20}$ alkyl, $C_2$-$C_{20}$ alkenyl, $C_2$-$C_{20}$ alkynyl, $C_3$-$C_{20}$ cycloalkyl, $C_3$-$C_{20}$ cycloalkenyl and $C_6$-$C_{18}$ aryl and X represents a chlorine, fluorine, bromine or iodine atom. The $C_1$-$C_{20}$ alkyl, $C_2$-$C_{20}$ alkenyl, $C_2$-$C_{20}$ alkynyl, $C_3$-$C_{20}$ cycloalkyl, $C_3$-$C_{20}$ cycloalkenyl and $C_6$-$C_{18}$ aryl substituents may be optionally substituted with one or more —OH, halogen, —NR$^a$C(O)R$^b$, —C(O)NR$^a$R$^b$—CN, —NO$_2$, —NR$^a$R$^b$, —OR$^a$, —SR$^a$, —CO$_2$R$^a$, —OC(O)OR$^a$, —OC(O)R$^a$, —C(O)H or —C(O)R$^a$ substituents in which R$^a$ and R$^b$ are as defined above.

The term "alcohol" refers to hydrocarbons or halohydrocarbons as defined above in which at least one hydrogen atom is replaced with a hydroxyl group —OH.

The term "ketone" refers to hydrocarbons comprising at least one or more carbonyl functional groups R$^c$—C(O)—R$^d$ in which R$^c$ and R$^d$ are, independently of each other, a $C_1$-$C_{20}$ alkyl, $C_2$-$C_{20}$ alkenyl, $C_2$-$C_{20}$ alkynyl, $C_3$-$C_{20}$ cycloalkyl, $C_3$-$C_{20}$ cycloalkenyl or $C_6$-$C_{18}$ aryl and may be optionally substituted with one or more —OH, halogen, —NR$^a$C(O)R$^b$, —C(O)NR$^a$R$^b$—CN, —NO$_2$, —NR$^a$R$^b$, —OR$^a$, —SR$^a$, —CO$_2$R$^a$, —OC(O)OR$^a$, —OC(O)R$^a$, —C(O)H, —C(O)R$^a$ substituents in which R$^a$ and R$^b$ are as defined above, R$^c$ and R$^d$ possibly being linked together to form, with the carbonyl group to which they are attached, a 4- to 10-membered and preferably 4- to 7-membered cyclic ketone. The cyclic ketone may also comprise one or more carbon-carbon double bonds. The cyclic ketone may also be optionally substituted with one or more substituents as defined above.

The term "amine" refers to hydrocarbons comprising at least one or more amine functional groups —NR$^c$R$^d$ in which R$^c$ and R$^d$ are as defined above, R$^c$ and R$^d$ possibly being linked together to form, with the nitrogen atom to which they are attached, a 4- to 10-membered aromatic or non-aromatic heterocycle.

The term "esters" refers to compounds of formula R—C(O)—O—R$^d$ in which R$^c$ and R$^d$ are as defined above, R$^c$ and R$^d$ possibly being linked together to form, with the ester group, a ring comprising from 4 to 20 carbon atoms.

The term "ether" refers to compounds of formula R$^c$—O—R$^d$ in which R$^c$ and R$^d$ are as defined above, R$^c$ and R$^d$ possibly being linked together to form, with the oxygen atom to which they are attached, a heterocycle comprising from 4 to 20 carbon atoms.

The term "aldehyde" refers to compounds comprising at least one or more —C(O)—H functional groups.

The term "nitrile" refers to compounds comprising at least one or more —CN functional groups.

The term "carbonate" refers to compounds of formula R$^c$—O—C(O)—O—R$^d$ in which R$^c$ and R$^d$ are as defined above.

The term "thioalkyl" refers to compounds of formula R$^c$SR$^d$ in which R$^c$ and R$^d$ are as defined above.

The term "amide" relates to compounds of formula R$^c$C(O)NR$^e$R$^d$ in which R$^c$ and R$^d$ are as defined above, R$^e$ being defined by the same substituents as those defining R$^c$, R$^c$ and R$^d$ possibly being linked together to form, with the amide group —C(O)N— to which they are attached, a 4- to 10-membered and preferably 4- to 7-membered cyclic amide. The cyclic amide may also comprise one or more carbon-carbon double bonds. The cyclic amide may also be optionally substituted with one or more substituents as defined above.

The term "heterocycle" denotes a 4- to 10-membered carbon-based ring, at least one of the ring members of which is a heteroatom chosen from the group consisting of O, S, P and N. The ring may comprise one or more carbon-carbon double bonds or one or more carbon-heteroatom double bonds or one or more heteroatoms-heteroatom double bonds. Preferably, the heterocycle may comprise 1, 2, 3, 4 or 5 heteroatoms as defined above. In particular, the heterocycle may comprise 1, 2 or 3 heteroatoms chosen from oxygen, nitrogen and sulfur. Preferably, the heterocycle may be a 4- to 6-membered carbon-based ring, 1, 2 or 3 ring members of which are heteroatoms chosen from O and N. The heterocycle may be optionally substituted with one or more substituents chosen from —OH, halogen, —NR$^a$C(O)R$^b$, —C(O)NR$^a$R$^b$—CN, —NO$_2$, —NR$^a$R$^b$, —OR$^a$, —SR$^a$, —CO$_2$R$^a$, —OC(O)OR$^a$, —OC(O)R$^a$, —C(O)H and —C(O)R$^a$ in which R$^a$ and R$^b$ are as defined above.

The term "organic extracting agent" refers to a compound comprising at least one carbon atom.

According to a first aspect, the invention relates to a process for purifying 2,3,3,3-tetrafluoro-1-propene (1234yf). The purification process is performed using a first composition comprising 2,3,3,3-tetrafluoro-1-propene, 1,1,1,2,2-pentafluoropropane (245cb) and trans-1,3,3,3-tetrafluoro-1-propene (1234ze-E).

Preferably, said process comprises the steps of:
a) placing said first composition in contact with at least one organic extracting agent to form a second composition;
b) extractive distillation of said second composition to form:
  i) a third composition comprising said organic extracting agent and trans-1,3,3,3-tetrafluoro-1-propene (1234ze-E); and
  ii) a stream comprising 2,3,3,3-tetrafluoro-1-propene and 1,1,1,2,2-pentafluoropropane (245cb);
c) recovery and separation of said third composition to form a stream comprising said organic extracting agent and a stream comprising trans-1,3,3,3-tetrafluoro-1-propene (1234ze-E).

Preferably, the stream comprising said organic extracting agent is recycled into step a). Preferably, the stream comprising trans-1,3,3,3-tetrafluoro-1-propene (1234ze-E) is purified or destroyed by incineration.

Preferably, said process also comprises a step of recovering said stream comprising 2,3,3,3-tetrafluoro-1-propene (1234yf) and 1,1,1,2,2-pentafluoropropane (245cb) obtained in step b), and of distilling said stream to form a stream A comprising 2,3,3,3-tetrafluoro-1-propene and a stream B comprising 1,1,1,2,2-pentafluoropropane (245cb).

Said first composition may comprise 2,3,3,3-tetrafluoro-1-propene, 1,1,1,2,2-pentafluoropropane (245cb), trans-1,3, 3,3-tetrafluoro-1-propene (1234ze-E) and at least one of the compounds chosen from the group consisting of chloromethane (40), 1,1-difluoroethane (152a), 1,1,1,2-tetrafluoroethane (134a), chloropentafluoroethane (115), trans-1,2,3,3,3-pentafluoropropene (1225ye-E), cis-1,2,3,3,3-pentafluoropropene (1225ye-Z) and 3,3,3-trifluoropropene (1243zf). Preferably, the first composition may comprise at least two, at least three, at least four, at least five, at least six or all of the compounds chosen from the group consisting of chloromethane (40), 1,1-difluoroethane (152a), 1,1,1,2-tetrafluoroethane (134a), chloropentafluoroethane (115), trans-1,2,3,3,3-pentafluoropropene (1225ye-E), cis-1,2,3,3,3-pentafluoropropene (1225ye-Z) and 3,3,3-trifluoropropene (1243zf).

When said first composition contains at least one of the compounds chosen from the group consisting of chloromethane (40), 1,1-difluoroethane (152a), 1,1,1,2-tetrafluoroethane (134a), chloropentafluoroethane (115), trans-1,2,3,3,3-pentafluoropropene (1225ye-E), cis-1,2,3,3,3-pentafluoropropene (1225ye-Z) and 3,3,3-trifluoropropene (1243zf), this or these compounds are contained in said second and third compositions.

Step c) of the present process may thus consist in recovering said third composition and in separating out, on the one hand, said organic extracting agent and, on the other hand, trans-1,3,3,3-tetrafluoro-1-propene (1234ze-E) and at least one of the compounds chosen from the group consisting of chloromethane (40), 1,1-difluoroethane (152a), 1,1,1,2-tetrafluoroethane (134a), chloropentafluoroethane (115), trans-1,2,3,3,3-pentafluoropropene (1225ye-E), cis-1,2,3,3,3-pentafluoropropene (1225ye-Z) and 3,3,3-trifluoropropene (1243zf).

Said first composition may comprise between 50% and 99% by weight of 2,3,3,3-tetrafluoro-1-propene relative to the total weight of the first composition, advantageously between 50% and 95% by weight, preferably between 55% and 90% and in particular between 60% and 80% by weight of 2,3,3,3-tetrafluoro-1-propene relative to the total weight of the first composition.

When it contains same, said first composition may comprise between 0.1% and 50% by weight of 1,1,1,2,2-pentafluoropropane (245cb) relative to the total weight of the first composition, advantageously between 0.1% and 49.9% by weight, preferably between 1% and 45% by weight, more preferably between 2% and 40% and in particular between 5% and 40% by weight of 1,1,1,2,2-pentafluoropropane (245cb) relative to the total weight of the first composition.

When it contains same, said first composition may comprise between 0.1% and 50% by weight of trans-1,3,3,3-tetrafluoro-1-propene (1234ze-E) relative to the total weight of the first composition, advantageously between 0.1% and 49.9% by weight, preferably between 0.5% and 40%, more preferentially between 1% and 30% by weight and in particular between 5% and 25% by weight of trans-1,3,3,3-tetrafluoro-1-propene (1234ze-E) relative to the total weight of the first composition.

When it contains same, said first composition may comprise less than 1% by weight of chloromethane (40) relative to the total weight of the first composition, advantageously between 1 and 5000 ppm by weight, preferably between 5 and 2000 ppm and in particular between 10 and 1000 ppm by weight of chloromethane (40) relative to the total weight of the first composition.

When it contains same, said first composition may comprise less than 2000 ppm by weight of 1,1-difluoroethane (152a) relative to the total weight of the first composition, advantageously between 1 and 1000 ppm by weight, preferably between 5 and 500 ppm and in particular between 10 and 250 ppm by weight of 1,1-difluoroethane (152a) relative to the total weight of the first composition.

When it contains same, said first composition may comprise less than 2000 ppm by weight of chloropentafluoroethane (115) relative to the total weight of the first composition, advantageously between 1 and 1000 ppm by weight, preferably between 5 and 500 ppm and in particular between 10 and 250 ppm by weight of chloropentafluoroethane (115) relative to the total weight of the first composition.

When it contains same, said first composition may comprise less than 2000 ppm by weight of 1,1,1,2-tetrafluoroethane (134a) relative to the total weight of the first composition, advantageously between 1 and 1000 ppm by weight, preferably between 5 and 500 ppm and in particular between 10 and 250 ppm by weight of 1,1,1,2-tetrafluoroethane (134a) relative to the total weight of the first composition.

When it contains same, said first composition may comprise less than 2000 ppm by weight of trans-1,2,3,3,3-pentafluoropropene (1225ye-E) relative to the total weight of the first composition, advantageously between 1 and 1000 ppm by weight, preferably between 5 and 500 ppm and in particular between 10 and 250 ppm by weight of trans-1,2,3,3,3-pentafluoropropene (1225ye-E) relative to the total weight of the first composition.

When it contains same, said first composition may comprise less than 2000 ppm by weight of cis-1,2,3,3,3-pentafluoropropene (1225ye-Z) relative to the total weight of the first composition, advantageously between 1 and 1000 ppm by weight, preferably between 5 and 500 ppm and in particular between 10 and 250 ppm by weight of cis-1,2,3,3,3-pentafluoropropene (1225ye-Z) relative to the total weight of the first composition.

When it contains same, said first composition may comprise less than 1% by weight of 3,3,3-trifluoropropene (1243zf) relative to the total weight of the first composition, advantageously between 1 and 5000 ppm by weight, preferably between 5 and 2000 ppm and in particular between 10 and 1500 ppm by weight of 3,3,3-trifluoropropene (1243zf) relative to the total weight of the first composition.

According to a particular embodiment, said organic extracting agent may be a solvent chosen from the group consisting of halohydrocarbon, alcohol, ketone, amine, ester, ether, aldehyde, nitrile, carbonate, thioalkyl, amide and heterocycle; or the organic extracting agent is triethylfluorosilane. Preferably, the organic extracting agent is chosen from the group consisting of amine, ether, ester, aldehyde, ketone, alcohol and heterocycle.

Preferably, the halohydrocarbons are chosen from the group consisting of bromofluoromethane, 1-bromo-1,2-difluoroethylene, 1,1,1-trifluoro-2-bromoethane, 2-chloropropane, bromoethane, iodomethane, 2-chloro-2-methylpropane, 2-bromopropane, chlorobromomethane, 3-bromopropene, 1-bromopropane, iodoethane, 2-bromo-2-methylpropane, 1-chloro-3-fluoropropane, 2-chloro-2-methylbutane, 1,2-dichloroethane, 2-iodopropane, dichlorobromomethane, 2-bromobutane, 1,2-dichloropropane, trichloroacetaldehyde, 1-chloro-4-fluorobutane, 1-bromo-3-fluoropropane, 1-bromobutane, 1-iodopropane, cis-1,3-dichloropropene, bromotrichloromethane, 1-bromo-2-chloroethane, 2-bromo-2-methylbutane, trans-1,3-dichloropropene, 1,1,2-trichloroethane, 2-bromopentane, 2,3-dichlorobutane, 1-bromo-3-methylbutane, 1,3-dichlorotrans-2-butene, 1,3-dichloropropane, 1,2-dibromo-1-fluoroethane, 1,2,2-trichloropropane, 2,3-dichloro-2-methylbutane, 1-bromopentane, 1,2-dichloro-2-butene, 1-iodobutane, 1,2-dibromoethane, 1,1,2-trichloropropane, 1,3-dichlorobutane, 1,2-dibromopropane, 1,2,3-trichloropropene, 1-chloro-3-bromopropane and tribromomethane.

Preferably, the alcohols are chosen from the group consisting of methanol, 2,2,2-trifluoroethanol, 1,1,1-trifluoro-2-propanol, ethanol, 2-propanol, tert-butanol, 2,2-difluoroethanol, propanol, 2-allyloxyethanol, 2-butanol, 2-methyl-2-butanol, isobutanol, 2,2,3,3-tetrafluoro-1-propanol, 2,2-dimethyl-1-propanol, 3-pentanol, 1-butanol, 1-methoxy-2-propanol, 1-(dimethylamino)-2-propanol, 3-methyl-3-pentanol, 1-chloro-2-methyl-2-propanol, 4,4,4-trifluorobutanol, 3-fluoropropanol, 2-chloroethanol, 2-methoxy-1-propanol, 1-ethoxy-2-propanol, 4-methyl-2-pentanol, 1,2-octanediol, 2-chloro-1-propanol, 2-(dimethylamino)ethanol, 3-hexanol, 2-hexanol, 2-ethoxy-1-propanol, 1-pentanol, 2,3-dimethylbutanol, 2-ethyl-1-butanol, 2-methyl-1-pentanol and 2-propoxyethanol.

Preferably, the ketones are chosen from the group consisting of 1,1,1-trifluoro-2-propanone, propanone, butanone, 3-pentanone, 2-pentanone, 3,3-dimethyl-2-butanone, 4-methyl-2-penta none, 2-hexanone, 5-hexen-2-one and 4-methyl-2-hexanone.

Preferably, the amines are chosen from the group consisting of ethylamine, isopropylamine, ethylmethylamine, 2-amino-2-methylpropane, n-propylamine, isopropylmethylamine, diethylamine, 2-butanamine, n-methylpropylamine, 1-butylamine, diisopropylamine, 3-methyl-2-butanamine, 3-pentylamine, n-methylbutylamine, 1-methoxy-2-propanamine, 2-methoxyethanamine, 2-methoxy-1-propanamine, n-pentylamine, n-methylhydroxylamine, dipropylamine, 2-ethoxyethanamine, n-methyl-1,2-ethanediamine, pyridine, 1,2-diaminoethane, 1,2-propanediamine, 2-ethylbutylamine, n-ethylethylenediamine, 1,1-diethoxy-n,n-dimethylmethanamine, 2-methylpyridine, 4-methyl-2-hexanamine, hexylamine, cyclohexylamine, n-ethyl-2-dimethylaminoethylamine, 1,3-propanediamine, 2-heptanamine, n,n-diethylethylenediamine, 2,6-dimethylpyridine, 4-methylpyridine and n,n'-diethyl-1,2-ethanediamine.

Preferably, the esters are chosen from the group consisting of methyl formate, methyl acetate, isopropyl formate, ethyl acetate, n-propyl formate, isopropyl acetate, tert-butyl acetate, ethyl propionate, sec-butyl acetate, diethyl carbonate, n-butyl acetate, bromoacetic acid methyl ester and methyl hexanoate.

Preferably, the ethers are chosen from the group consisting of 2,2,2-trifluoroethyl methyl ether, 2-methoxy-1-propene, diethyl ether, ethoxyethene, dimethoxymethane, methyl cyclopropyl ether, 2-ethoxypropane, methyl t-butyl ether, chloromethoxymethane, diisopropyl ether, 2-ethoxy-2-methylpropane, 2-ethoxybutane, 1-methoxy-2-methylbutane, 2,2-dimethoxypropane, 1-ethoxy-2-methylpropane, 1,2-dimethoxyethane, diethoxymethane, di-n-propyl ether, 1-ethoxybutane, 1-methoxypentane, 1,2-dimethoxypropane, isopropyl isobutyl ether, 1,1-diethoxyethane, trimethoxymethane, 2,2-diethoxypropane, isobutyl tert-butyl ether, sec-butyl tert-butyl ether, 1,1-diethoxypropane, 2-methoxyethanol, 2-chloro-1,1-dimethoxyethane, methoxycyclohexane, ethoxyethanol, di-n-butyl ether, 1-ethoxyhexane, 1,1,1-triethoxyethane and 1-methoxy-2-acetoxypropane.

Preferably, the aldehydes are chosen from the group consisting of acetaldehyde, ethanedial, isobutanal, methylglyoxal, 2-methylbutanal, 2,6-dimethyl-5-heptenal and hexanal.

Preferably, the nitriles are chosen from the group consisting of acetonitrile, propionitrile, butyronitrile, valeronitrile and (methyleneamino)acetonitrile.

Preferably, the carbonate is diethyl carbonate.

Preferably, the amide is ethanethioamide.

Preferably, the thioalkyls are chosen from the group consisting of ethanethiol, dimethyl sulfide, 2-propanethiol, 4-methoxy-2-methyl-2-butanethiol, tert-butylthiol, 1-propanethiol, 2-butanethiol, 2-methyl-1-propanethiol, diethyl sulfide, butanethiol, 3-mercapto-1,2-propanediol, tetrahydrothiophene and 1-pentanethiol.

Preferably, the heterocycles are chosen from the group consisting of tetrahydrofuran, dioxane, 1,3-dioxane, 1,3,5-trioxane, n-methylmorpholine, 2-methylpyrazine, n-ethylmorpholine, 1-methylpiperazine, 1,2-epoxypropane, piperidine, 3-furfural and 2,6-dimethylmorpholine.

Said organic extracting agent may be ethylamine, bromofluoromethane, 1-bromo-1,2-difluoroethylene, acetaldehyde, 1,1,1-trifluoro-2-propanone, 1,1,1-trifluoro-2-bromoethane, 2,2,2-trifluoroethyl methyl ether, isopropylamine, methyl formate, 2-methoxy-1-propene, diethyl ether, 1,2-epoxypropane, ethanethiol, ethoxyethene, ethylmethylamine, dimethyl sulfide, 2-chloropropane, bromoethane, dimethoxymethane, iodomethane, 2-amino-2-methylpropane, methyl cyclopropyl ether, n-propylamine, isopropylmethylamine, ethanedial, 2-chloro-2-methylpropane, 2-propanethiol, 2-ethoxypropane, methyl t-butyl ether, diethylamine, propanone, methyl acetate, 4-methoxy-2-methyl-2-butanethiol, 2-bromopropane, chloromethoxymethane, 2-butanamine, n-methylpropylamine, tert-butylthiol, isobutanal, methanol, tetrahydrofuran, 1-propanethiol, chlorobromomethane, isopropyl formate, diisopropyl ether, 3-bromopropene, 1-bromopropane, methylglyoxal, iodoethane, 2-ethoxy-2-methylpropane, 2-bromo-2-methylpropane, 2,2,2-trifluoroethanol, 1-chloro-3-fluoropropane, 1,1,1-trifluoro-2-propanol, 1-butylamine, ethyl acetate, ethanol, butanone, n-propyl formate, 2-ethoxybutane, 2-propanol, acetonitrile, tert-butanol, 1-methoxy-2-methylbutane, 2,2-dimethoxypropane, 2-chloro-2-methylbutane, 1,2-dichloroethane, 1-ethoxy-2-methylpropane, diisopropylamine, 2-butanethiol, 1,2-dimethoxyethane, 3-methyl-2-butanamine, diethoxymethane, 2-methyl-1-propanethiol, isopropyl acetate, 2-iodopropane, di-n-propyl ether, 3-pentylamine, n-methylbutylamine, 2-bromobutane, diethyl sulfide, 1-ethoxybutane, 1-methoxy-2-propanamine, 2-methylbutanal, 2-methoxyethanamine, 2,2-difluoroethanol, 1,2-dichloropropane, propanol, tert-butyl acetate, propionitrile, trichloroacetaldehyde, 2-allyloxyethanol, butanethiol, 1-methoxypentane, ethyl propionate, 2-butanol, 1,2-dimethoxypropane, isopropyl isobutyl ether, 1-chloro-4-fluorobutane, 1-bromo-3-fluoropropane, dioxane, 1-bromobutane, 3-pentanone, 1,1-diethoxyethane, 2-pentanone, 2-methyl-2-butanol, 1-iodopropane, 2-methoxy-1-propanamine, trimethoxymethane, cis-1,3-dichloropropene, n-pentylamine, 3,3-dimethyl-2-butanone, 1,3-dioxane, piperidine, 1-bromo-2-chloroethane, isobutanol, 2-bromo-2-methylbutane, dipropylamine, 2,2,3,3-tetraflouro-1-propanol, 2-ethoxyethanamine, triethylfluorosilane, sec-butyl acetate, trans-1,3-dichloropropene, 2,2-dimethyl-1-propanol, n-methyl-1,2-ethanediamine, 2,2-diethoxypropane, 1,3,5-trioxane, pyridine, n-methylmorpholine, 3-pentanol, 4-methyl-2-pentanone, 1,2-diaminoethane, isobutyl tert-butyl ether, 2-bromopentane, butyronitrile, 1-butanol, 2,3-dichlorobutane, sec-butyl tert-butyl ether, 1-methoxy-2-propanol, 1,2-propanediamine, 2,6-dimethyl-5-heptenal, 1-bromo-3-methylbutane, 1,3-dichloro-trans-2-butene, 1,3-dichloropropane, 1-(dimethylamino)-2-propanol, tetrahydrothiophene, 3-methyl-3-pentanol, 1,2-dibromo-1-fluoroethane, 1,1-diethoxypropane, 1,2,2-trichloropropane, 1-chloro-2-methyl-2-propanol, 2-methoxyethanol, 4,4,4-trifluorobutanol, 2-ethylbutylamine, diethyl carbonate, n-butyl acetate, 1-pentanethiol, 2-chloro-1,1-dimethoxyethane, 2-hexanone, n-ethylethylenediamine, 3-fluoropropanol, 5-hexen-2-one, 2,3-dichloro-2-methylbutane, 1,1-diethoxy-n,n-dimethylmethanamine, 2-methylpyridine, 1-bromopentane, 2-methoxy-1-propanol, 1,2-dichloro-2-butene, 1-iodobutane, hexanal, 1-ethoxy-2-propanol, 1,2-dibromoethane, 4-methyl-2-pentanol, bromoacetic acid methyl ester, 1,1,2-trichloropropane, 1,2-octanediol, 4-methyl-2-hexanamine, hexylamine, 2-chloro-1-propanol, methoxycyclohexane, 2-(dimethylamino)ethanol, 1,3-dichlorobutane, cyclohexylamine, n-ethyl-2-dimethylaminoethylamine, ethoxyethanol, 3-hexanol, 2-hexanol, 2-methylpyrazine, 2-ethoxy-1-propanol, 1-pentanol, n-ethylmorpholine, 1-methylpiperazine, 1,3-propanediamine, di-n-butyl ether, valeronitrile, (methyleneamino)acetonitrile, 1,2-dibromopropane, 1,2,3-trichloropropene, 2-heptanamine, 2,3-dimethylbutanol, 1-ethoxyhexane, 1-chloro-3-bromopropane, n,n-diethylethylenediamine, 3-furfural, 2,6-dimethylpyridine, 4-methyl-2-hexanone, 1,1,1-triethoxyethane, 1-methoxy-2-acetoxypropane, 4-methylpyridine, n,n'-diethyl-1,2-ethanediamine, 2,6-dimethylmorpholine, 2-ethyl-1-butanol, 2-methyl-1-pentanol, methyl hexanoate, 2-propoxyethanol, 1-propoxy-2-propanol or dimethylethanolamine.

Advantageously, said organic extracting agent may be ethylamine, bromofluoromethane, acetaldehyde, isopropylamine, methyl formate, 2-methoxy-1-propene, diethyl ether, 1,2-epoxypropane, ethanethiol, ethoxyethene, ethylmethylamine, dimethyl sulfide, bromoethane, dimethoxymethane, 2-amino-2-methylpropane, methyl cyclopropyl ether, n-propylamine, isopropylmethylamine, 2-propanethiol, 2-ethoxypropane, methyl t-butyl ether, diethylamine, propanone, methyl acetate, 4-methoxy-2-methyl-2-butanethiol, 2-bromopropane, 2-butanamine, n-methylpropylamine, tert-butylthiol, isobutanal, tetrahydrofuran, 1-propanethiol, isopropyl formate, diisopropyl ether, 1-bromopropane, methylglyoxal, 2-ethoxy-2-methylpropane, 2-bromo-2-methylpropane, 1-butylamine, ethyl acetate, butanone, n-propyl formate, 2-ethoxybutane, 2-propanol, tert-butanol, 1-methoxy-2-methylbutane, 2,2-dimethoxypropane, 1-ethoxy-2-methylpropane, diisopropylamine, 2-butanethiol, 1,2-dimethoxyethane, 3-methyl-2-butanamine, diethoxymethane, 2-methyl-1-propanethiol, isopropyl acetate, 2-iodopropane, di-n-propyl ether, 3-pentylamine, n-methylbutylamine, 2-bromobutane, diethyl sulfide, 1-ethoxybutane, 1-methoxy-2-propanamine, 2-methylbutanal, 2-methoxyethanamine, propanol, tert-butyl acetate, propionitrile, 2-allyloxyethanol, butanethiol, 1-methoxypentane, ethyl propionate, 2-butanol, 1,2-dimethoxypropane, isopropyl isobutyl ether, 1-bromo-3-fluoropropane, dioxane, 1-bromobutane, 3-pentanone, 1,1-diethoxyethane, 2-pentanone, 2-methyl-2-butanol, 2-methoxy-1-propanamine, trimethoxymethane, n-pentylamine, 3,3-dimethyl-2-butanone, 1,3-dioxane, piperidine, isobutanol, 2-bromo-2-methylbutane, dipropylamine, 2-ethoxyethanamine, sec-butyl acetate, 2,2-dimethyl-1-propanol, n-methyl-1,2-ethanediamine, 2,2-diethoxypropane, 1,3,5-trioxane, pyridine, n-methylmorpholine, 3-pentanol, 4-methyl-2-pentanone, 1,2-diaminoethane, isobutyl tert-butyl ether, 2-bromopentane, butyronitrile, 1-butanol, sec-butyl tert-butyl ether, 1-methoxy-2-propanol, 1,2-propanediamine, 2,6-dimethyl-5-heptenal, 1-bromo-3-methylbutane, 1-(dimethylamino)-2-propanol, tetrahydrothiophene, 3-methyl-3-pentanol, 1,1-diethoxypropane, 2-methoxyethanol, 2-ethylbutylamine, diethyl carbonate, n-butyl acetate, 1-pentanethiol, 2-chloro-1,1-dimethoxyethane, 2-hexanone, n-ethylethylenediamine, 5-hexen-2-one, 1,1-diethoxy-n,n-dimethylmethanamine, 2-methylpyridine, 1-bromopentane, 2-methoxy-1-propanol, hexanal, 1-ethoxy-2-propanol, 4-methyl-2-pentanol, 1,2-octanediol, 4-methyl-2-hexanamine, hexylamine, methoxycyclohexane, 2-(dimethylamino)ethanol, cyclohexylamine, n-ethyl-2-dimethylaminoethylamine, ethoxyethanol, 3-hexanol, 2-hexanol, 2-methylpyrazine, 2-ethoxy-1-propanol, 1-pentanol, n-ethylmorpholine, 1-methylpiperazine, 1,3-propanediamine, di-n-butyl-ether, valeronitrile, (methyleneamino)acetonitrile, 2-heptanamine, 2,3-dimethylbutanol, 1-ethoxyhexane, n,n-diethylethylenediamine, 3-furfural, 2,6-dimethylpyridine, 4-methyl-2-hexanone, 1,1,1-triethoxyethane, 1-methoxy-2-acetoxypropane, 4-methylpyridine, n,n'-diethyl-1,2-ethanediamine, 2,6-dimethylmorpholine, 2-ethyl-1-butanol, 2-methyl-1-pentanol, methyl hexanoate, 2-propoxyethanol, 1-propoxy-2-propanol or dimethylethanolamine.

Preferably, said organic extracting agent may be ethylamine, acetaldehyde, isopropylamine, methyl formate, diethyl ether, 1,2-epoxypropane, ethylmethylamine, dimethoxymethane, 2-amino-2-methylpropane, methyl cyclopropyl ether, n-propylamine, isopropylmethylamine, 2-ethoxypropane, methyl t-butyl ether, diethylamine, propanone, methyl acetate, 4-methoxy-2-methyl-2-butanethiol, 2-butanamine, n-methylpropylamine, isobutanal, tetrahydrofuran, isopropyl formate, diisopropyl ether, 2-ethoxy-2-methylpropane, 1-butylamine, ethyl acetate, buta none, n-propyl formate, 2-ethoxybutane, 1-methoxy-2-methylbutane, 2,2-dimethoxypropane, 1-ethoxy-2-methylpropane, diisopropylamine, 1,2-dimethoxyethane, 3-methyl-2-butanamine, diethoxymethane, isopropyl acetate, di-n-propyl ether, 3-pentylamine, n-methylbutylamine, diethyl sulfide, 1-ethoxybutane, 1-methoxy-2-propanamine, 2-methylbutanal, 2-methoxyethanamine, tert-butyl acetate, propionitrile, 2-allyloxyethanol, 1-methoxypentane, ethyl propionate, 1,2-dimethoxypropane, isopropyl isobutyl ether, dioxane, 3-pentanone, 1,1-diethoxyethane, 2-pentanone, 2-methoxy-1-propanamine, trimethoxymethane, n-pentylamine, 3,3-dimethyl-2-butanone, 1,3-dioxane, piperidine, dipropylamine, 2-ethoxyethanamine, sec-butyl acetate, n-methyl-1,2-ethanediamine, 2,2-diethoxypropane, pyridine, n-methylmorpholine, 4-methyl-2-pentanone, 1,2-diaminoethane, isobutyl tert-butyl ether, butyronitrile, sec-butyl tert-butyl ether, 1-methoxy-2-propanol, 1,2-propanediamine, 2,6-dimethyl-5-heptenal, 1-(dimethylamino)-2-propanol, 3-methyl-3-pentanol, 1,1-diethoxypropane, 2-ethylbutylamine, diethyl carbonate, n-butyl acetate, 2-hexanone, n-ethylethylenediamine, 5-hexen-2-one, 1,1-diethoxy-n,n-dimethylmethanamine, 2-methylpyridine, 2-methoxy-1-propanol, hexanal, 1-ethoxy-2-propanol, 4-methyl-2-hexanamine, hexylamine, methoxycyclohexane, 2-(dimethylamino)ethanol, cyclohexylamine, n-ethyl-2-dimethylaminoethylamine, ethoxyethanol, 2-methylpyrazine, 2-ethoxy-1-propanol, n-ethylmorpholine, 1-methylpiperazine, 1,3-propanediamine, di-n-butyl ether, valeronitrile, 2-heptanamine, 1-ethoxyhexane, n,n-diethylethylenediamine, 2,6-dimethylpyridine, 4-methyl-2-hexanone, 1,1,1-triethoxyethane, 1-methoxy-2-acetoxypropane, 4-methylpyridine, n,n'-diethyl-1,2-ethanediamine, 2,6-dimethylmorpholine, methyl hexanoate, 2-propoxyethanol or 1-propoxy-2-propanol.

In particular, said organic extracting agent may be ethylamine, isopropylamine, diethyl ether, ethylmethylamine, 2-amino-2-methylpropane, n-propylamine, isopropylmethylamine, 2-ethoxypropane, methyl t-butyl ether, diethylamine, propanone, methyl acetate, 2-butanamine, n-methylpropylamine, isobutanal, tetrahydrofuran, 1-butylamine, ethyl acetate, butanone, n-propyl formate, 2,2-dimethoxypropane, 1-ethoxy-2-methylpropane, 1,2-dimethoxyethane, 3-methyl-2-butanamine, diethoxymethane, isopropyl acetate, 3-pentylamine, n-methylbutylamine, 1-ethoxybutane, 1-methoxy-2-propanamine, 2-methylbutanal, 2-methoxyethanamine, tert-butyl acetate, 1-methoxypentane, ethyl propionate, 1,2-dimethoxypropane, dioxane, 3-pentanone, 1,1-diethoxyethane, 2-pentanone, 2-methoxy-1-propanamine, trimethoxymethane, n-pentylamine, 3,3-dimethyl-2-butanone, 1,3-dioxane, piperidine, 2-ethoxyethanamine, sec-butyl acetate, n-methyl-1,2-ethanediamine, 2,2-diethoxypropane, 4-methyl-2-pentanone, 1,2-diaminoethane, butyronitrile, 1-methoxy-2-propanol, 1,2-propanediamine, 2,6-dimethyl-5-heptenal, 1-(dimethylamino)-2-propanol, 1,1-diethoxypropane, 2-ethylbutylamine, diethyl carbonate, n-butyl acetate, 2-hexanone, n-ethylethylenediamine, 5-hexen-2-one, 2-methylpyridine, 2-methoxy-1-propanol, hexanal, 1-ethoxy-2-propanol, 4-methyl-2-hexanamine, hexylamine, methoxycyclohexane, 2-(dimethylamino)ethanol, cyclohexylamine, n-ethyl-2-dimethylaminoethylamine, 2-methylpyrazine, 2-ethoxy-1-propanol, 1-methylpiperazine, 1,3-propanediamine, di-n-butyl ether, valeronitrile, 2-heptanamine, 1-ethoxyhexane, n,n-diethylethylenediamine, 2,6-dimethylpyridine, 4-methyl-2-hexanone, 1,1,1-triethoxyethane, 1-methoxy-2-acetoxypropane, 4-methylpyridine, n,n'-diethyl-1,2-ethanediamine, 2,6-dimethylmorpholine, methyl hexanoate, 2-propoxyethanol or 1-propoxy-2-propanol.

The organic extracting agent to be used may be chosen as a function of the compounds present in said first composition. Thus, the organic extracting agent may be chosen as a function of the separation factor and of the absorption capacity established for a particular composition. Besides these two criteria, the choice of the organic extracting agent may be optionally based on other commercial or environmental criteria, for instance the cost of the organic extracting agent, its availability on the market, and its toxicity or flammability properties. Furthermore, according to a particular embodiment, in order to optimize the functioning of the distillation columns used in the steps b) and c) of the present process for purifying 2,3,3,3-tetrafluoro-1-propene, the boiling point of the organic extracting agent may be from 0° C. to 200° C., advantageously from 10° C. to 190° C., preferably from 10° C. to 180° C., in particular from 10° C. to 170° C., preferentially from 10° C. to 160° C. and more preferentially from 10° C. to 150° C.

According to a preferred embodiment, said organic extracting agent has a separation factor $S_{1,2}$ of greater than or equal to 1.1, said separation factor being calculated by the formula $S_{1,2}=(\gamma_{1,S}*P1)/(\gamma_{2,S}*P2)$ in which
- $\gamma_{1,S}$ represents the activity coefficient of 2,3,3,3-tetrafluoro-1-propene (1234yf) in said organic extracting agent at infinite dilution;
- P1 represents the saturating vapor pressure of 2,3,3,3-tetrafluoro-1-propene (1234yf);
- $\gamma_{2,S}$ represents the activity coefficient of trans-1,3,3,3-tetrafluoro-1-propene (1234ze-E) in said organic extracting agent at infinite dilution;
- P2 represents the saturating vapor pressure of trans-1,3,3,3-tetrafluoro-1-propene (1234ze-E).

According to a preferred embodiment, said organic extracting agent has a separation factor $S_{1,2}$ of greater than or equal to 1.1, said separation factor being calculated by the formula $S_{1,2}=(\gamma_{1,S}*P1)/(\gamma_{2,S}*P2)$ in which
- $\gamma_{1,S}$ represents the activity coefficient of 1,1,1,2,2-pentafluoropropane (245cb) in said organic extracting agent at infinite dilution;
- P1 represents the saturating vapor pressure of 1,1,1,2,2-pentafluoropropane (245cb);
- $\gamma_{2,S}$ represents the activity coefficient of trans-1,3,3,3-tetrafluoro-1-propene (1234ze-E) in said organic extracting agent at infinite dilution;
- P2 represents the saturating vapor pressure of trans-1,3,3-tetrafluoro-1-propene (1234ze-E).

According to a preferred embodiment, said organic extracting agent has:
- a separation factor $S_{1,2}$ of greater than or equal to 1.1, said separation factor being calculated by the formula $S_{1,2}=(\gamma_{1,S}*P1)/(\gamma_{2,S}*P2)$ in which
  - $\gamma_{1,S}$ represents the activity coefficient of 2,3,3,3-tetrafluoro-1-propene (1234yf) in said organic extracting agent at infinite dilution;
  - P1 represents the saturating vapor pressure of 2,3,3,3-tetrafluoro-1-propene (1234yf);
  - $\gamma_{2,S}$ represents the activity coefficient of trans-1,3,3,3-tetrafluoro-1-propene (1234ze-E) in said organic extracting agent at infinite dilution;
  - P2 represents the saturating vapor pressure of trans-1,3,3-tetrafluoro-1-propene (1234ze-E);

and

- a separation factor $S_{1,2}$ of greater than or equal to 1.1, said separation factor being calculated by the formula $S_{1,2}=(\gamma_{1,S}*P1)/(\gamma_{2,S}*P2)$ in which
  - $\gamma_{1,S}$ represents the activity coefficient of 1,1,1,2,2-pentafluoropropane (245cb) in said organic extracting agent at infinite dilution;
  - P1 represents the saturating vapor pressure of 1,1,1,2,2-pentafluoropropane (245cb);
  - $\gamma_{2,S}$ represents the activity coefficient of trans-1,3,3,3-tetrafluoro-1-propene (1234ze-E) in said organic extracting agent at infinite dilution;
  - P2 represents the saturating vapor pressure of trans-1,3,3-tetrafluoro-1-propene (1234ze-E).

Advantageously, in the two cases, the separation factor $S_{1,2}$ may be greater than or equal to 1.2, preferably greater than or equal to 1.4, more preferentially greater than or equal to 1.6, in particular greater than or equal to 1.8, more particularly greater than or equal to 2.0.

According to a preferred embodiment, said organic extracting agent has an absorption capacity $C_{2,S}$ of greater than or equal to 0.20, said absorption capacity being calculated by the formula $C_{2,S}=1/(\gamma_{2,S})$ in which $\gamma_{2,S}$ represents the activity coefficient of trans-1,3,3,3-tetrafluoro-1-propene (1234ze-E) in said organic extracting agent at infinite dilution. Advantageously, the absorption capacity $C_{2,S}$ is greater than or equal to 0.40, preferably greater than or equal to 0.60, more preferentially greater than or equal to 0.80, in particular greater than or equal to 1.0.

According to a preferred embodiment, said organic extracting agent may have a separation factor $S_{1,2}$ of greater than or equal to 1.1, advantageously greater than or equal to 1.2, preferably greater than or equal to 1.4, more preferentially greater than or equal to 1.6, in particular greater than or equal to 1.8 and more particularly greater than or equal to 2.0; and an absorption capacity $C_{2,S}$ of greater than or equal to 0.20, advantageously greater than or equal to 0.40, preferably greater than or equal to 0.60, more preferentially greater than or equal to 0.80 and in particular greater than or equal to 1.0.

Since trans-1,3,3,3-tetrafluoro-1-propene (1234ze-E) is one of the main impurities to be removed, the separation factor and said absorption capacity may be calculated for the particular binary couple consisting of 2,3,3,3-tetrafluoro-1-propene and trans-1,3,3,3-tetrafluoro-1-propene (1234ze-E) and/or 1,1,1,2,2-pentafluoropropane (245cb) and trans-1,3,3,3-tetrafluoro-1-propene (1234ze-E). The separation factor $S_{1,2}$ makes it possible to determine the capacity of an organic extracting agent to separate two or more compounds. The absorption capacity $C_{2,S}$ makes it possible to determine the amount of solvent to be used to obtain separation between the compounds under consideration.

Said organic extracting agent may have a separation factor $S_{1,2}$ of greater than or equal to 1.4, said separation factor being calculated by the formula $S_{1,2}=(\gamma_{1,S}*P1)/(\gamma_{2,S}*P2)$ in which $\gamma_{1,S}$ represents the activity coefficient of 2,3,3,3-tetrafluoro-1-propene relative to said organic extracting agent, P1 represents the saturating vapor pressure of 2,3,3,3-tetrafluoro-1-propene, $\gamma_{2,S}$ represents the activity coefficient of trans-1,3,3,3-tetrafluoro-1-propene in said organic extracting agent at infinite dilution, P2 represents the saturating vapor pressure of trans-1,3,3,3-tetrafluoro-1-propene and/or said organic extracting agent may have a separation factor $S_{1,2}$ of greater than or equal to 1.4, said separation factor being calculated by the formula $S_{1,2}=(\gamma_{1,S}*P1)/(\gamma_{2,S}*P2)$ in which $\gamma_{1,S}$ represents the activity coefficient of 1,1,1,2,2-pentafluoropropane (245cb) relative to said organic extracting agent, P1 represents the saturating vapor pressure of 1,1,1,2,2-pentafluoropropane (245cb), $\gamma_{2,S}$ represents the activity coefficient of trans-1,3,3,3-tetrafluoro-1-propene in said organic extracting agent at infinite dilution, P2 represents the saturating vapor pressure of trans-1,3,3,3-tetrafluoro-1-propene; and, preferably, said organic extracting agent may have an absorption capacity $C_{2,S}$ of greater than or equal to 0.60, said absorption capacity being calculated by the formula $C_{2,S}=1/(\gamma_{2,S})$ in which $\gamma_{2,S}$ represents the activity coefficient of trans-1,3,3,3-tetrafluoro-1-propene in said organic extracting agent at infinite dilution; said organic extracting agent may thus be ethylamine, acetaldehyde, isopropylamine, methyl formate, diethyl ether, 1,2-epoxypropane, ethylmethylamine, dimethoxymethane, 2-amino-2-methylpropane, methyl cyclopropyl ether, n-propylamine, isopropylmethylamine, 2-ethoxypropane, methyl t-butyl ether, diethylamine, propanone, methyl acetate, 4-methoxy-2-methyl-2-butanethiol, 2-butanamine, n-methylpropylamine, isobutanal, tetrahydrofuran, isopropyl formate, diisopropyl ether, 2-ethoxy-2-methylpropane, 1-butylamine, ethyl acetate, butanone, n-propyl formate, 2-ethoxybutane, 1-methoxy-2-methylbutane, 2,2-dimethoxypropane, 1-ethoxy-2-methylpropane, diisopropylamine, 1,2-dimethoxyethane, 3-methyl-2-butanamine, diethoxymethane, isopropyl acetate, di-n-propyl ether, 3-pentylamine, n-methylbutylamine, diethyl sulfide, 1-ethoxybutane, 1-methoxy-2-propanamine, 2-methylbutanal, 2-methoxyethanamine, tert-butyl acetate, propionitrile, 2-allyloxyethanol, 1-methoxypentane, ethyl propionate, 1,2-dimethoxypropane, isopropyl isobutyl ether, dioxane, 3-pentanone, 1,1-diethoxyethane, 2-pentanone, 2-methoxy-1-propanamine, trimethoxymethane, n-pentylamine, 3,3-dimethyl-2-butanone, 1,3-dioxane, piperidine, dipropylamine, 2-ethoxyethanamine, sec-butyl acetate, n-methyl-1,2-ethanediamine, 2,2-diethoxypropane, pyridine, n-methylmorpholine, 4-methyl-2-pentanone, 1,2-diaminoethane, isobutyl tert-butyl ether, butyronitrile, sec-butyl tert-butyl ether, 1-methoxy-2-propanol, 1,2-propanediamine, 2,6-dimethyl-5-heptenal, 1-(dimethylamino)-2-propanol, 3-methyl-3-pentanol, 1,1-diethoxypropane, 2-ethylbutylamine, diethyl carbonate, n-butyl acetate, 2-hexanone, n-ethylethylenediamine, 5-hexen-2-one, 1,1-diethoxy-n,n-dimethylmethanamine, 2-methylpyridine, 2-methoxy-1-propanol, hexanal, 1-ethoxy-2-propanol, 4-methyl-2-hexanamine, hexylamine, methoxycyclohexane, 2-(dimethylamino)ethanol, cyclohexylamine, n-ethyl-2-dimethylaminoethylamine, ethoxyethanol, 2-methylpyrazine, 2-ethoxy-1-propanol, n-ethylmorpholine, 1-methylpiperazine, 1,3-propanediamine, di-n-butyl ether, valeronitrile, 2-heptanamine, 1-ethoxyhexane, n,n-diethylethylenediamine, 2,6-dimethylpyridine, 4-methyl-2-hexanone, 1,1,1-triethoxyethane, 1-methoxy-2-acetoxypropane, 4-methylpyridine, n,n'-diethyl-1,2-ethanediamine, 2,6-dimethylmorpholine, methyl hexanoate, 2-propoxyethanol or 1-propoxy-2-propanol.

Said organic extracting agent may have a separation factor $S_{1,2}$ of greater than or equal to 1.6, said separation factor being calculated by the formula $S_{1,2}=(\gamma_{1,S}*P1)/(\gamma_{2,S}*P2)$ in which $\gamma_{1,S}$ represents the activity coefficient of 2,3,3,3-tetrafluoro-1-propene relative to said organic extracting agent, P1 represents the saturating vapor pressure of 2,3,3,3-tetrafluoro-1-propene, $\gamma_{2,S}$ represents the activity coefficient of trans-1,3,3,3-tetrafluoro-1-propene in said organic extracting agent at infinite dilution, P2 represents the saturating vapor pressure of trans-1,3,3,3-tetrafluoro-1-propene and/or said organic extracting agent may have a separation factor $S_{1,2}$ of greater than or equal to 1.6, said separation factor being calculated by the formula $S_{1,2}=(\gamma_{1,S}*P1)/(\gamma_{2,S}*P2)$ in which $\gamma_{1,S}$ represents the activity coefficient of 1,1,1,2,2-pentafluoropropane (245cb) relative to said organic extracting agent, P1 represents the saturating vapor pressure of 1,1,1,2,2-pentafluoropropane (245cb), $\gamma_{2,S}$ represents the activity coefficient of trans-1,3,3,3-tetrafluoro-1-propene in said organic extracting agent at infinite dilution, P2 represents the saturating vapor pressure of trans-1,3,3,3-tetrafluoro-1-propene; and, preferably, said organic extracting agent may have an absorption capacity $C_{2,S}$ of greater than or equal to 0.80, said absorption capacity being calculated by the formula $C_{2,S}=1/(\gamma_{2,S})$ in which $\gamma_{2,S}$ represents the activity coefficient of trans-1,3,3,3-tetrafluoro-1-propene in said organic extracting agent at infinite dilution; said organic extracting agent may thus be ethylamine, isopropylamine, diethyl ether, ethylmethylamine, 2-amino-2-methylpropane, n-propylamine, isopropylmethylamine, 2-ethoxypropane, methyl t-butyl ether, diethylamine, propanone, methyl acetate, 2-butanamine, n-methylpropylamine, isobutanal, tetrahydrofuran, 1-butylamine, ethyl acetate, butanone, n-propyl formate, 2,2-dimethoxypropane, 1-ethoxy-2-methylpropane, 1,2-dimethoxyethane, 3-methyl-2-butanamine, diethoxymethane, isopropyl acetate, 3-pentylamine, n-methylbutylamine, 1-ethoxybutane, 1-methoxy-2-propanamine, 2-methylbutanal, 2-methoxyethanamine, tert-butyl acetate, 1-methoxypentane, ethyl propionate, 1,2-dimethoxypropane, dioxane, 3-pentanone, 1,1-diethoxyethane, 2-pentanone, 2-methoxy-1-propanamine, trimethoxymethane, n-pentylamine, 3,3-dimethyl-2-butanone, 1,3-dioxane, piperidine, 2-ethoxyethanamine, sec-butyl acetate, n-methyl-1,2-ethanediamine, 2,2-diethoxypropane, 4-methyl-2-pentanone, 1,2-diaminoethane, butyronitrile, 1-methoxy-2-propanol, 1,2-propanediamine, 2,6-dimethyl-5-heptenal, 1-(dimethylamino)-2-propanol, 1,1-diethoxypropane, 2-ethylbutylamine, diethyl carbonate, n-butyl acetate, 2-hexanone, n-ethylethylenediamine, 5-hexen-2-one, 2-methylpyridine, 2-methoxy-1-propanol, hexanal, 1-ethoxy-2-propanol, 4-methyl-2-hexanamine, hexylamine, methoxycyclohexane, 2-(dimethylamino)ethanol, cyclohexylamine, n-ethyl-2-dimethylaminoethylamine, 2-methylpyrazine, 2-ethoxy-1-propanol, 1-methylpiperazine, 1,3-propanediamine, di-n-butyl ether, valeronitrile, 2-heptanamine, 1-ethoxyhexane, n,n-diethylethylenediamine, 2,6-dimethylpyridine, 4-methyl-2-hexanone, 1,1,1-triethoxyethane, 1-methoxy-2-acetoxypropane, 4-methylpyridine, n,n'-diethyl-1,2-ethanediamine, 2,6-dimethylmorpholine, methyl hexanoate, 2-propoxyethanol or 1-propoxy-2-propanol.

Preferably, said organic extracting agent may be ethylamine, isopropylamine, diethyl ether, ethylmethylamine, 2-amino-2-methylpropane, n-propylamine, isopropylmethylamine, 2-ethoxypropane, methyl t-butyl ether, diethylamine, propanone, methyl acetate, 2-butanamine, n-methylpropylamine, isobutanal, tetrahydrofuran, 1-butylamine, ethyl acetate, butanone, n-propyl formate, 2,2-dimethoxypropane, 1-ethoxy-2-methylpropane, 1,2-dimethoxyethane, 3-methyl-2-butanamine, diethoxymethane, isopropyl acetate, 3-pentylamine, n-methylbutylamine, 1-ethoxybutane, 1-methoxy-2-propanamine, 2-methylbutanal, 2-methoxyethanamine, tert-butyl acetate, 1-methoxypentane, ethyl propionate, 1,2-dimethoxypropane, dioxane, 3-pentanone, 1,1-diethoxyethane, 2-pentanone, 2-methoxy-1-propanamine, trimethoxymethane, n-pentylamine, 3,3-dimethyl-2-butanone, 1,3-dioxane, piperidine, 2-ethoxyethanamine, sec-butyl acetate, n-methyl-1,2-ethanediamine, 2,2-diethoxypropane, 4-methyl-2-pentanone, 1,2-diaminoethane, butyronitrile, 1-methoxy-2-propanol, 1,2-propanediamine, 2,6-dimethyl-5-heptenal, 1-(dimethylamino)-2-propanol, 1,1-diethoxypropane, 2-ethylbutylamine, diethyl carbonate, n-butyl acetate, 2-hexanone, n-ethylethylenediamine, 5-hexen-2-one, 2-methylpyridine, 2-methoxy-1-propanol or hexanal. In particular, said organic extracting agent may be ethylamine, isopropylamine, diethyl ether, ethylmethylamine, 2-amino-2-methylpropane, n-propylamine, isopropylmethylamine, 2-ethoxypropane, diethylamine, 2-butanamine, n-methylpropylamine, 1-butylamine, n-propyl formate, 2,2-dimethoxypropane, 1-ethoxy-2-methylpropane, 3-methyl-2-butanamine, diethoxymethane, isopropyl acetate, 3-pentylamine, n-methylbutylamine, 1-ethoxybutane, 1-methoxy-2-propanamine, 2-methylbutanal, 2-methoxyethanamine, tert-butyl acetate, 1-methoxypentane, 1,2-dimethoxypropane, dioxane, 1-diethoxyethane, 2-methoxy-1-propanamine, trimethoxymethane, n-pentylamine, 1,3-dioxane, piperidine, 2-ethoxyethanamine, sec-butyl acetate, n-methyl-1,2-ethanediamine, 2,2-diethoxypropane, 1,2-diaminoethane, butyronitrile, 1-methoxy-2-propanol, 1,2-propanediamine, 2,6-dimethyl-5-heptenal, 1-(dimethylamino)-2-propanol, 1,1-diethoxypropane, 2-ethylbutylamine, n-butyl acetate, n-ethylethylenediamine, 5-hexen-2-one, 2-methylpyridine, 2-methoxy-1-propanol or hexanal.

According to a preferred embodiment, said organic extracting agent may be ethylamine, isopropylamine, diethyl ether, n-propylamine, diethylamine, propanone, methyl acetate, butanone, diethoxymethane, isopropyl acetate, 3-pentylamine, 2-methoxyethanamine, tert-butyl acetate, dioxane, 1,1-diethoxyethane, trimethoxymethane, n-pentylamine, 1,3-dioxane, sec-butyl acetate, 1,2-diaminoethane, 1-methoxy-2-propanol, 1,2-propanediamine, n-butyl acetate, 2-methoxy-1-propanol or hexanal. In particular, said organic extracting agent may be ethylamine, isopropylamine, diethyl ether, n-propylamine, diethylamine, diethoxymethane, isopropyl acetate, 3-pentylamine, 2-methoxyethanamine, tert-butyl acetate, dioxane, 1,1-diethoxyethane, trimethoxymethane, n-pentylamine, 1,3-dioxane, sec-butyl acetate, 1,2-diaminoethane, 1-methoxy-2-propanol, 1,2-propanediamine, n-butyl acetate, 2-methoxy-1-propanol or hexanal.

According to a preferred embodiment, said third composition comprising said organic extracting agent and trans-1,3,3,3-tetrafluoro-1-propene (1234ze-E); preferably, the third composition comprising said organic extracting agent and trans-1,3,3,3-tetrafluoro-1-propene (1234ze-E) and optionally or not at least one of the compounds chosen from the group consisting of chloromethane (40), 1,1-difluoroethane (152a), 1,1,1,2-tetrafluoroethane (134a), chloropentafluoroethane (115), trans-1,2,3,3,3-pentafluoropropene (1225ye-E), cis-1,2,3,3,3-pentafluoropropene (1225ye-Z) and 3,3,3-trifluoropropene (1243zf); may be subjected to distillation to separate the organic extracting agent and trans-1,3,3,3-tetrafluoro-1-propene (1234ze-E); preferably, to separate, on the one hand, the organic extracting agent, and, on the other hand, trans-1,3,3,3-tetrafluoro-1-propene (1234ze-E) and optionally or not at least one of the compounds chosen from the group consisting of chloromethane (40), 1,1-difluoroethane (152a), 1,1,1,2-tetrafluoroethane (134a), chloropentafluoroethane (115), trans-1,2,3,3,3-pentafluoropropene (1225ye-E), cis-1,2,3,3,3-pentafluoropropene (1225ye-Z) and 3,3,3-trifluoropropene (1243zf). Said organic extracting agent is thus recycled into step a) of the purification process. The stream comprising trans-1,3,3,3-tetrafluoro-1-propene (1234ze-E) and optionally or not at least one of the compounds chosen from the group consisting of chloromethane (40), 1,1-difluoroethane (152a), 1,1,1,2-tetrafluoroethane (134a), chloropentafluoroethane (115), trans-1,2,3,3,3-pentafluoropropene (1225ye-E), cis-1,2,3,3,3-pentafluoropropene (1225ye-Z) and 3,3,3-trifluoropropene (1243zf) either may be subjected to one or more subsequent purification steps or may be destroyed by incineration.

The present process thus makes it possible to purify 2,3,3,3-tetrafluoro-1-propene (1234yf). Advantageously, the content of trans-1,3,3,3-tetrafluoro-1-propene (1234ze-E) in the stream comprising 2,3,3,3-tetrafluoro-1-propene (1234yf) and 1,1,1,2,2-pentafluoropropane (245cb), obtained in step b) of the present purification process, is less than the content thereof in said first composition. Preferably, the content of trans-1,3,3,3-tetrafluoro-1-propene (1234ze-E) and/or of at least one of the compounds chosen from the group consisting of chloromethane (40), 1,1-difluoroethane (152a), 1,1,1,2-tetrafluoroethane (134a), chloropentafluoroethane (115), trans-1,2,3,3,3-pentafluoropropene (1225ye-E), cis-1,2,3,3,3-pentafluoropropene (1225ye-Z) and 3,3,3-trifluoropropene (1243zf) in the stream comprising 2,3,3,3-tetrafluoro-1-propene (1234yf) and 1,1,1,2,2-pentafluoropropane (245cb), obtained in step b) of the present purification process, is less than the content thereof in said first composition.

For example, the content of trans-1,3,3,3-tetrafluoro-1-propene (1234ze-E) or of any of the compounds chosen from the group consisting of chloromethane (40), 1,1-difluoroethane (152a), 1,1,1,2-tetrafluoroethane (134a), chloropentafluoroethane (115), trans-1,2,3,3,3-pentafluoropropene (1225ye-E), cis-1,2,3,3,3-pentafluoropropene (1225ye-Z) and 3,3,3-trifluoropropene (1243zf) may be reduced by 50%, advantageously by 75%, preferably by 90%, in particular by 95% and more particularly by 98%. Advantageously, the content of at least two, at least three, at least four, at least five, at least six or of all of the compounds chosen from the group consisting of chloromethane (40), 1,1-difluoroethane (152a), 1,1,1,2-tetrafluoroethane (134a), chloropentafluoroethane (115), trans-1,2,3,3,3-pentafluoropropene (1225ye-E), cis-1,2,3,3,3-pentafluoropropene (1225ye-Z) and 3,3,3-trifluoropropene (1243zf) may be reduced by 50%, advantageously by 75%, preferably by 90%, in particular by 95% and more particularly by 98%. Preferably, the content of trans-1,3,3,3-tetrafluoro-1-propene (1234ze-E) may be reduced by 50%, advantageously by 75%, preferably by 90%, in particular by 95% and more particularly by 98%.

Preferably, the stream comprising 2,3,3,3-tetrafluoro-1-propene and 1,1,1,2,2-pentafluoropropane obtained in step b) of the present purification process may be free of trans-1,3,3,3-tetrafluoro-1-propene (1234ze-E). In particular, the stream comprising 2,3,3,3-tetrafluoro-1-propene and 1,1,1,2,2-pentafluoropropane obtained in step b) of the present purification process may be free of trans-1,3,3,3-tetrafluoro-1-propene (1234ze-E) and/or optionally of at least one, at least two, at least three, at least four, at least five, at least six or of all of the compounds chosen from the group consisting of chloromethane (40), 1,1-difluoroethane (152a), 1,1,1,2-tetrafluoroethane (134a), chloropentafluoroethane (115), trans-1,2,3,3,3-pentafluoropropene (1225ye-E), cis-1,2,3,3,3-pentafluoropropene (1225ye-Z) and 3,3,3-trifluoropropene (1243zf) when this or these compounds are present in said first composition. The term "free of" means that the stream comprising 2,3,3,3-tetrafluoro-1-propene (1234yf) comprises less than 50 ppm, advantageously less than 20 ppm and preferably less than 10 ppm of the compound under consideration relative to the total weight of the stream. The contents are expressed on a weight basis.

According to a preferred embodiment, said first composition used in step a) of the present process may be purified before being used. Specifically, if said first composition comprises impurities with a boiling point below the boiling point of 2,3,3,3-tetrafluoro-1-propene and optionally heavy impurities, the process may comprise, prior to step a), the following steps:

i') use of a composition comprising 2,3,3,3-tetrafluoro-1-propene, impurities with a boiling point below the boiling point of 2,3,3,3-tetrafluoro-1-propene, 1,1,1,2,2-pentafluoropropane (245cb), and trans-1,3,3,3-tetrafluoro-1-propene (1234ze-E), optionally or not at least one compound chosen from the group consisting of chloromethane (40), 1,1-difluoroethane (152a), 1,1,1,2-tetrafluoroethane (134a), chloropentafluoroethane (115), trans-1,2,3,3,3-pentafluoropropene (1225ye-E), cis-1,2,3,3,3-pentafluoropropene (1225ye-Z), 3,3,3-trifluoropropene (1243zf), and optionally or not heavy impurities;

ii') distillation of said composition from step i) to remove, at the top of the column, impurities with a boiling point below the boiling point of 2,3,3,3-tetrafluoro-1-propene and to form a first stream comprising 2,3,3,3-tetrafluoro-1-propene, 1,1,1,2,2-pentafluoropropane (245cb) and trans-1,3,3,3-tetrafluoro-1-propene (1234ze-E), optionally or not at least one compound chosen from the group consisting of chloromethane (40), 1,1-difluoroethane (152a), 1,1,1,2-tetrafluoroethane (134a), chloropentafluoroethane (115), trans-1,2,3,3,3-pentafluoropropene (1225ye-E), cis-1,2,3,3,3-pentafluoropropene (1225ye-Z), 3,3,3-trifluoropropene (1243zf), and optionally or not heavy impurities, recovered at the bottom of the distillation column;

iii') optionally or not, distillation of said first stream recovered at the bottom of the distillation column in step ii') to recover, at the top of the column, a second stream comprising 2,3,3,3-tetrafluoro-1-propene, 1,1,1,2,2-pentafluoropropane (245cb) and trans-1,3,3,3-tetrafluoro-1-propene (1234ze-E), and optionally or not at least one compound chosen from the group consisting of chloromethane (40), 1,1-difluoroethane (152a), 1,1,1,2-tetrafluoroethane (134a), chloropentafluoroethane (115), trans-1,2,3,3,3-pentafluoropropene (1225ye-E), cis-1,2,3,3,3-pentafluoropropene (1225ye-Z) and 3,3,3-trifluoropropene (1243zf), and, at the bottom of the distillation column, a stream comprising the heavy impurities;

said at first stream recovered in step ii') or said second stream recovered in step iii') corresponding to said first composition used in step a).

According to a second aspect, the present invention provides a process for producing 2,3,3,3-tetrafluoro-1-propene. In addition, this process may include the purification thereof. Thus, the present invention provides a process for producing 2,3,3,3-tetrafluoro-1-propene, comprising the steps of:

A) fluorination in the presence of a catalyst for a compound of formula (I) $CX(Y)_2$—$CX(Y)_m$—$CH_mXY$ in which X and Y independently represent a hydrogen, fluorine or chlorine atom and m=0 or 1; and/or catalytic fluorination in the presence of a catalyst for a compound of formula $(CX_nY_{3-n})CH_pX_{1-p}CH_mX_{2-m}$ (II) in which X is, independently of each other, Cl, F, I or Br; Y is, independently of each other, H, Cl, F, I or Br; n is 1, 2 or 3; and m is 0, 1 or 2; and p is 0 or 1;

B) recovery of a stream comprising 2,3,3,3-tetrafluoro-1-propene, 1,1,1,2,2-pentafluoropropane (245cb), trans-1,3,3,3-tetrafluoro-1-propene (1234ze-E) and optionally or not at least one of the compounds chosen from the group consisting of chloromethane (40), 1,1-difluoroethane (152a), 1,1,1,2-tetrafluoroethane (134a), chloropentafluoroethane (115), trans-1,2,3,3,3-pentafluoropropene (1225ye-E), cis-1,2,3,3,3-pentafluoropropene (1225ye-Z) and 3,3,3-trifluoropropene (1243zf);

C) implementation of the process for purifying 2,3,3,3-tetrafluoro-1-propene according to the present invention using the stream recovered in step B).

According to a preferred embodiment, the process for producing 2,3,3,3-tetrafluoro-1-propene comprising the steps of:

A) fluorination in the presence of a catalyst for a compound of formula (I) $CX(Y)_2$—$CX(Y)_m$—$CH_mXY$ in which X and Y independently represent a hydrogen, fluorine or chlorine atom and m=0 or 1; and/or catalytic fluorination in the presence of a catalyst for a compound of formula $(CX_nY_{3-n})CH_pX_{1-p}CH_mX_{2-m}$ (II) in which X is, independently of each other, Cl, F, I or Br; Y is, independently of each other, H, Cl, F, I or Br; n is 1, 2 or 3; and m is 0, 1 or 2; and p is 0 or 1;

B) recovery of a stream comprising 2,3,3,3-tetrafluoro-1-propene, 1,1,1,2,2-pentafluoropropane (245cb), trans-1,3,3,3-tetrafluoro-1-propene (1234ze-E) and optionally or not at least one of the compounds chosen from the group consisting of chloromethane (40), 1,1-difluoroethane (152a), 1,1,1,2-tetrafluoroethane (134a), chloropentafluoroethane (115), trans-1,2,3,3,3-pentafluoropropene (1225ye-E), cis-1,2,3,3,3-pentafluoropropene (1225ye-Z) and 3,3,3-trifluoropropene (1243zf);

C) implementation of the process for purifying 2,3,3,3-tetrafluoro-1-propene using the stream recovered in step B) and comprising the steps of:
  a) placing the stream recovered in step B) in contact with at least one organic extracting agent to form a second composition;
  b) extractive distillation of said second composition to form:

i) a third composition comprising said organic extracting agent, trans-1,3,3,3-tetrafluoro-1-propene (1234ze-E) and optionally or not said at least one of the compounds chosen from the group consisting of chloromethane (40), 1,1-difluoroethane (152a), 1,1,1,2-tetrafluoroethane (134a), chloropentafluoroethane (115), trans-1,2,3,3,3-pentafluoropropene (1225ye-E), cis-1,2,3,3,3-pentafluoropropene (1225ye-Z) and 3,3,3-trifluoropropene (1243zf); and ii) a stream comprising 2,3,3,3-tetrafluoro-1-propene and 1,1,1,2,2-pentafluoropropane;

c) recovery and separation of said third composition to form, on the one hand, a stream comprising said organic extracting agent and, on the other hand, a stream comprising trans-1,3,3,3-tetrafluoro-1-propene (1234ze-E) and optionally or not at least one of the compounds chosen from the group consisting of chloromethane (40), 1,1-difluoroethane (152a), 1,1,1,2-tetrafluoroethane (134a), chloropentafluoroethane (115), trans-1,2,3,3,3-pentafluoropropene (1225ye-E), cis-1,2,3,3,3-pentafluoropropene (1225ye-Z) and 3,3,3-trifluoropropene (1243zf).

Preferably, the stream comprising said organic extracting agent may be recycled into step a). Preferably, the stream comprising trans-1,3,3,3-tetrafluoro-1-propene (1234ze-E) and optionally or not at least one of the compounds chosen from the group consisting of chloromethane (40), 1,1-difluoroethane (152a), 1,1,1,2-tetrafluoroethane (134a), chloropentafluoroethane (115), trans-1,2,3,3,3-pentafluoropropene (1225ye-E), cis-1,2,3,3,3-pentafluoropropene (1225ye-Z) and 3,3,3-trifluoropropene (1243zf) may be purified or destroyed by incineration.

According to a particular embodiment, the stream recovered in step B) of the process for producing 2,3,3,3-tetrafluoro-1-propene may comprise hydrofluoric acid. In this case, prior to step C), the stream recovered in step B) may undergo a preliminary distillation B1') to remove HF at the bottom of the distillation column. A stream comprising 2,3,3,3-tetrafluoro-1-propene, 1,1,1,2,2-pentafluoropropane, trans-1,3,3,3-tetrafluoro-1-propene (1234ze-E) and optionally or not at least one of the compounds chosen from the group consisting of chloromethane (40), 1,1-difluoroethane (152a), 1,1,1,2-tetrafluoroethane (134a), chloropentafluoroethane (115), trans-1,2,3,3,3-pentafluoropropene (1225ye-E), cis-1,2,3,3,3-pentafluoropropene (1225ye-Z) and 3,3,3-trifluoropropene (1243zf) is recovered at the top of the distillation column. The latter stream recovered at the top of the distillation column is then subjected to step C) of the process for producing 2,3,3,3-tetrafluoro-1-propene.

According to a particular embodiment, the stream recovered in step B) of the process for producing 2,3,3,3-tetrafluoro-1-propene may comprise impurities with a boiling point below the boiling point of 2,3,3,3-tetrafluoro-1-propene. In this case, prior to step C), the stream recovered in step B) may undergo a preliminary distillation B2'), subsequent to step B1'), to remove, at the top of the distillation column, said impurities with a boiling point below the boiling point of 2,3,3,3-tetrafluoro-1-propene and to form a first stream comprising 2,3,3,3-tetrafluoro-1-propene, 1,1,1,2,2-pentafluoropropane, trans-1,3,3,3-tetrafluoro-1-propene (1234ze-E) and optionally or not at least one of the compounds chosen from the group consisting of chloromethane (40), 1,1-difluoroethane (152a), 1,1,1,2-tetrafluoroethane (134a), chloropentafluoroethane (115), trans-1,2,3,3,3-pentafluoropropene (1225ye-E), cis-1,2,3,3,3-pentafluoropropene (1225ye-Z) and 3,3,3-trifluoropropene (1243zf), recovered at the bottom of the distillation column. The latter stream recovered at the bottom of the distillation column is then subjected to step C) of the process for producing 2,3,3,3-tetrafluoro-1-propene.

According to a particular embodiment, the stream recovered in step B) of the process for producing 2,3,3,3-tetrafluoro-1-propene may comprise heavy impurities. In this case, prior to step C), the stream recovered in step B) may undergo a preliminary distillation B3'), subsequent to step B1') and/or B2'), to remove, at the bottom of the distillation column, said heavy impurities; and to form a first stream comprising 2,3,3,3-tetrafluoro-1-propene, 1,1,1,2,2-pentafluoropropane, trans-1,3,3,3-tetrafluoro-1-propene (1234ze-E) and optionally or not at least one of the compounds chosen from the group consisting of chloromethane (40), 1,1-difluoroethane (152a), 1,1,1,2-tetrafluoroethane (134a), chloropentafluoroethane (115), trans-1,2,3,3,3-pentafluoropropene (1225ye-E), cis-1,2,3,3,3-pentafluoropropene (1225ye-Z) and 3,3,3-trifluoropropene (1243zf), recovered at the top of the distillation column. The latter stream recovered at the top of the distillation column is then subjected to step C) of the process for producing 2,3,3,3-tetrafluoro-1-propene.

According to a particular embodiment, the stream recovered in step B) of the process for producing 2,3,3,3-tetrafluoro-1-propene may also comprise HCl. The hydrochloric acid may be recovered by distillation before or after step B1', independently of the other steps of the process.

More particularly, step A) is performed using 1,1,2,3-tetrachloropropene, 2,3,3,3,-tetrachloropropene, 1,1,3,3-tetrachloropropene, 1,3,3,3-tetrachloropropene, 1,1,1,2,3-pentachloropropane, 1,1,1,3,3-pentachloropropane, 1,1,2,2,3-pentachloropropane, 1,2-dichloro-3,3,3-trifluoropropane, 2-chloro-2,3,3,3-tetrafluoropropane, 1,1,1,2,2-pentafluoropropane, 1-chloro-1,3,3,3-tetrafluoropropane and 1,1,1,3,3-pentafluoropropane, preferably using 1,1,1,2,3-pentachloropropane, 1,1,2,3,tetrachloropropene, 1,1,1,2,2-pentafluoropropane and/or 2-chloro-3,3,3-trifluoro-1-propene; in particular using 1,1,1,2,3-pentachloropropane (240db).

FIG. 1 represents a simplified scheme of a device for performing a process for purifying 2,3,3,3-tetrafluoro-1-propene and 1,1,1,2,2-pentafluoropropane according to a particular embodiment of the invention. The mixture derived from the fluorination reaction, in the presence of a catalyst, a compound of formula (I) $CX(Y)_2$—$CX(Y)_m$—$CH_mXY$ as defined in the present invention; and/or catalytic fluorination, in the presence of a catalyst, a compound of formula $(CX_nY_{3-n})CH_pX_{1-p}$=$CH_mX_{2-m}$ (II) as defined in the present invention, is obtained at 1. In this particular embodiment, the mixture comprises 2,3,3,3-tetrafluoro-1-propene, 1,1,1,2,2-pentafluoropropane (245cb), trans-1,3,3,3-tetrafluoro-1-propene (1234ze-E) and impurities with a boiling point below the boiling point of 2,3,3,3-tetrafluoro-1-propene. The mixture is transferred into a distillation column 2 via pipe 3. The impurities with a boiling point below the boiling point of 2,3,3,3-tetrafluoro-1-propene are recovered at the top of distillation column 2 and conveyed via pipe 5 to an incinerator or a purification device 15. The residue obtained at the bottom of the distillation column and comprising the other constituents of the mixture is conveyed to a second extractive distillation column 6 via pipe 4. The extractive distillation performed at 6 is directed toward separating 2,3,3,3-tetrafluoro-1-propene and 1,1,1,2,2-pentafluoropropane (245cb) from the other constituents of the mixture. The extractive distillation column 6 is fed with the organic extracting agent 10. The stream comprising 2,3,3,3-tetrafluoro-1-propene and 1,1,1,2,2-pentafluoropropane (245cb) is recovered at the top of the distillation column 6 and conveyed to the distillation column 12 via pipe 7. The organic extracting agent 10 and trans-1,3,3,3-tetrafluoro-1-propene (1234ze-E) are recovered at the bottom of the distillation column 6 and conveyed to the distillation column 9 where they are separated. The organic extracting agent is recovered at the bottom of the distillation column 9 and recycled into the extractive distillation column 6 via pipe 11. The trans-1,3,3,3-tetrafluoro-1-propene is recovered at the top of the distillation column 9 and conveyed to an incinerator or a purification device 15. The distillation column 12 allows separation between the 2,3,3,3-tetrafluoro-1-propene recovered at the top of the distillation column 13 and the 1,1,1,2,2-pentafluoropropane recovered at the bottom of the distillation column 14. The 1,1,1,2,2-pentafluoropropane may be recycled into reactor 23 described in FIG. 2 below.

Figure 1B:
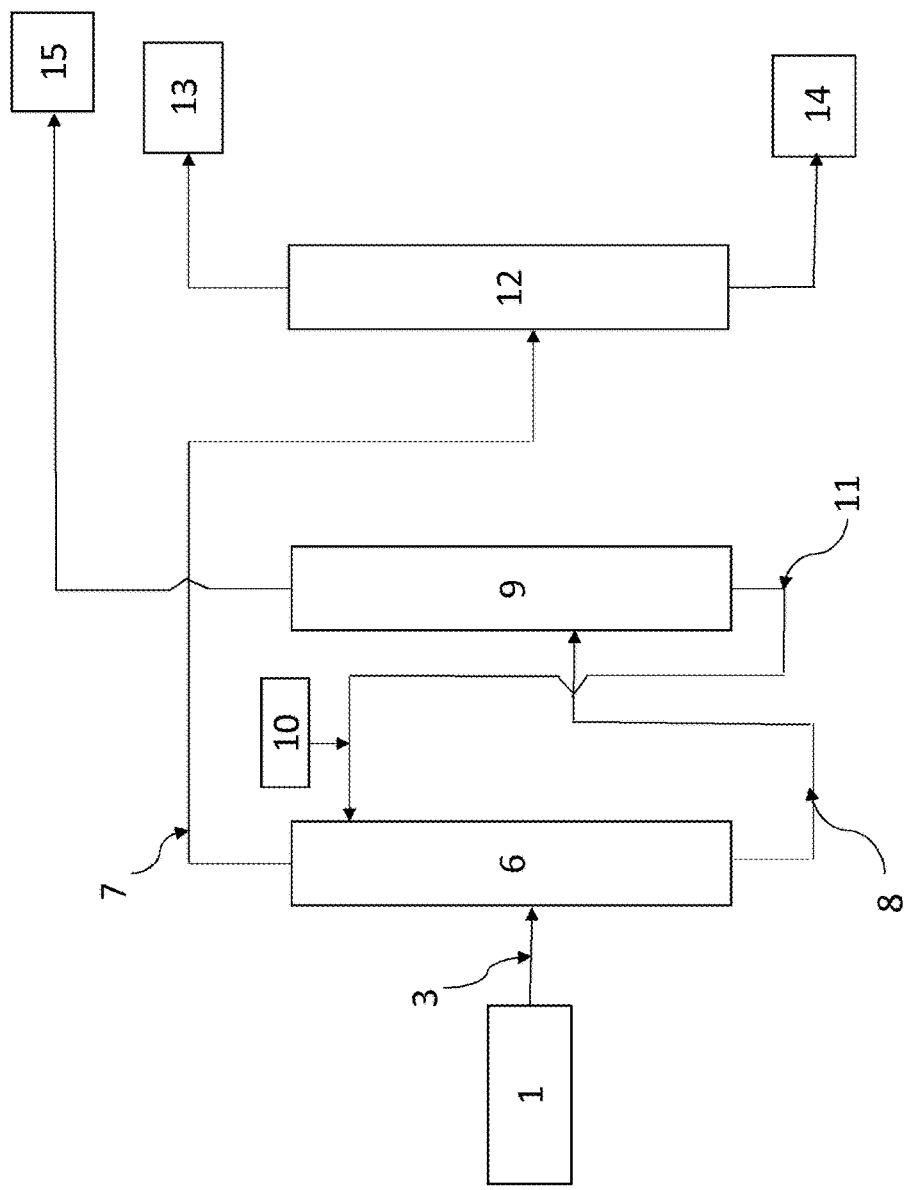
Figure 1C:
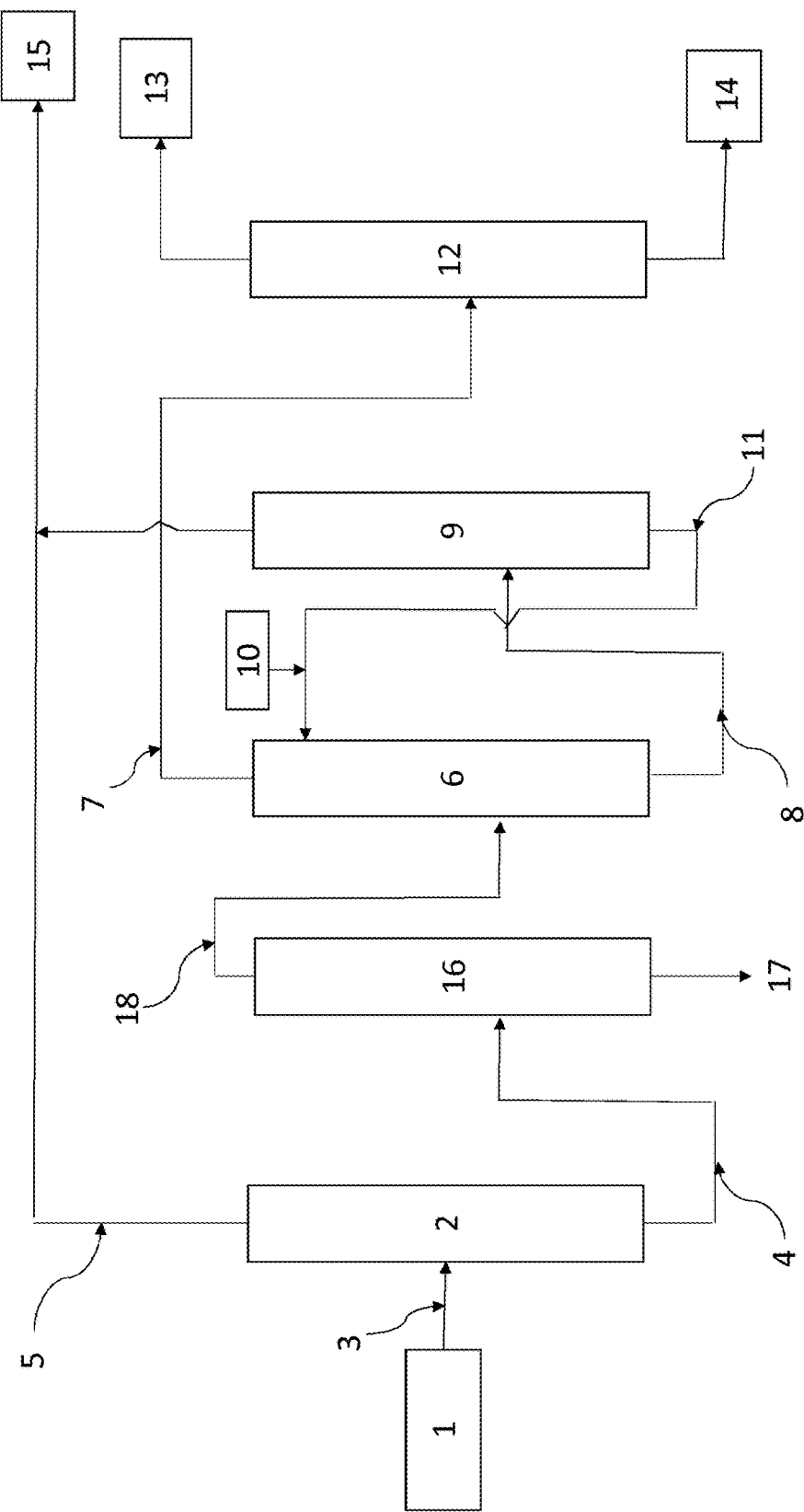

The mixture provided in 1 may be free of impurities with a boiling point below that of 2,3,3,3-tetrafluoro-1-propene. In this case, as illustrated in FIG. 1b, the mixture 1 is conveyed via pipe 3 to the extractive distillation column 6 to be processed as explained above in relation with FIG. 1a. In another particular embodiment illustrated in FIG. 1c, the mixture 1 may comprise heavy impurities. In this case, distillation may be performed using the stream obtained at the bottom of the distillation column 2. This stream is thus conveyed via pipe 4 to the distillation column 16. The heavy impurities are recovered at the bottom of the distillation column 17. The stream recovered at the top of the distillation column 16 comprises 2,3,3,3-tetrafluoro-1-propene, 1,1,1,2,2-pentafluoropropane (245cb) and trans-1,3,3,3-tetrafluoro-1-propene (1234ze-E). This stream is transferred via pipe 18 to the extractive distillation column 6 to be processed therein as explained above in relation with FIG. 1a. The mixture obtained at 1 may also comprise at least one of the compounds chosen from the group consisting of chloromethane (40), 1,1-difluoroethane (152a), 1,1,1,2-tetrafluoroethane (134a), chloropentafluoroethane (115), trans-1,2,3,3,3-pentafluoropropene (1225ye-E), cis-1,2,3,3,3-pentafluoropropene (1225ye-Z) and 3,3,3-trifluoropropene (1243zf). These compounds are found in the same stream as the trans-1,3,3,3-tetrafluoro-1-propene (1234ze-E). They are thus absorbed by the organic extracting agent during the extractive distillation 6 to be conveyed to the distillation column 9 where they are recovered at the top of the distillation column with the trans-1,3,3,3-tetrafluoro-1-propene (1234ze-E) and are incinerated or purified at 15.

Figure 2:
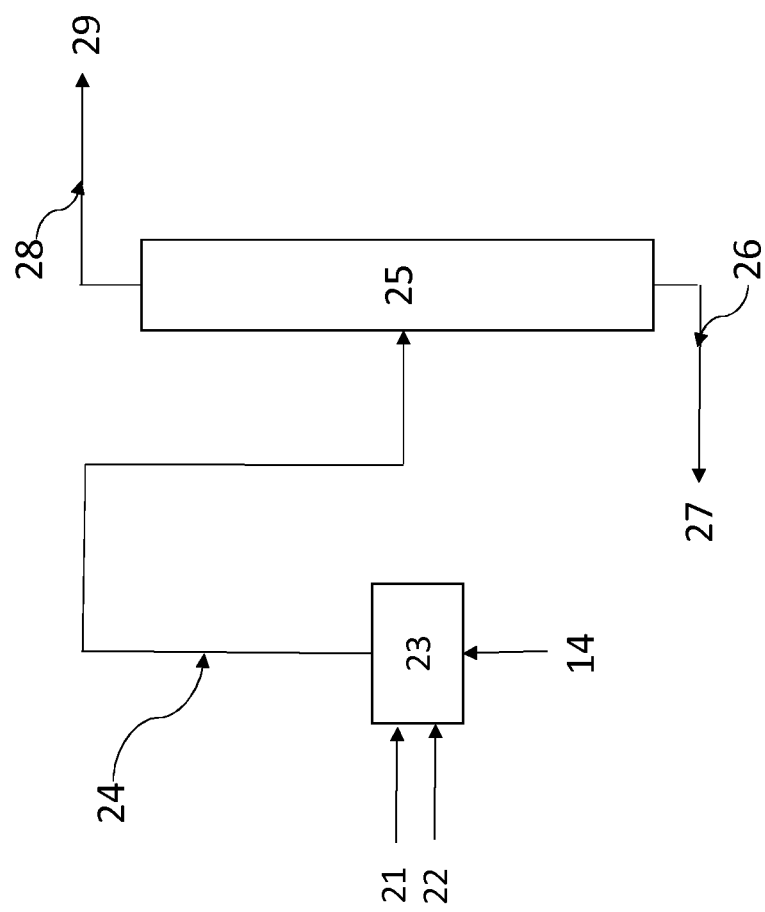
FIG. 2 schematically represents a device for performing a process for producing 2,3,3,3-tetrafluoro-1-propene according to a particular embodiment of the present invention.

FIG. 2 schematically illustrates a device for performing a process for producing 2,3,3,3-tetrafluoropropene according to a particular embodiment of the present invention. Hydrofluoric acid 21 is placed in contact with 1,1,1,2,3-pentachloropropane (240db) 22 in a reactor 23. The reactor 23 may also be fed with the stream 14 comprising 1,1,1,2,2-pentafluoropropane (245cb) and originating from the recycling of the process for purifying 2,3,3,3-tetrafluoro-1-propene and 1,1,1,2,2-pentafluoropropane (245cb). The mixture obtained, comprising 2,3,3,3-tetrafluoro-1-propene, 1,1,1,2,2-pentafluoropropane (245cb), trans-1,3,3,3-tetrafluoro-1-propene (1234ze-E) and optionally or not at least one of the compounds chosen from the group consisting of chloromethane (40), 1,1-difluoroethane (152a), 1,1,1,2-tetrafluoroethane (134a), chloropentafluoroethane (115), trans-1,2,3,3,3-pentafluoropropene (1225ye-E), cis-1,2,3,3,3-pentafluoropropene (1225ye-Z) and 3,3,3-trifluoropropene (1243zf), is recovered at the reactor outlet and conveyed to a distillation column 25 via pipe 24. The mixture may also comprise HCl, HF and heavy impurities or impurities with a boiling point below that of 2,3,3,3-tetrafluoro-1-propene. The stream obtained at the bottom of the distillation column comprising HF and optionally heavy impurities is conveyed to the purification device 27 via pipe 26 to purify HF which will optionally be recycled in 23. The other constituents of the mixture are conveyed via pipe 28 to a device 29 for purifying 2,3,3,3-tetrafluoro-1-propene and 1,1,1,2,2-pentafluoropropane. The purification device 29 may be any of the devices illustrated in FIGS. 1a-1c.

The catalyst used in the present process for producing 2,3,3,3-tetrafluoropropene may be based, for example, on a metal comprising a transition metal oxide or a derivative or a halide or an oxyhalide of such a metal. Mention may be made, for example, of $FeCl_3$, chromium oxyfluoride, chromium oxides (optionally subjected to fluorination treatments) and chromium fluorides, and mixtures thereof. Other possible catalysts are catalysts supported on carbon, antimony-based catalysts, and aluminum-based catalysts (for example $AlF_3$ and $Al_2O_3$, aluminum oxyfluoride and aluminum fluoride).

Use may be made in general of a chromium oxyfluoride, an aluminum fluoride or oxyfluoride, or an optionally supported catalyst containing a metal such as Cr, Ni, Fe, Zn, Ti, V, Zr, Mo, Ge, Sn, Pb, Mg or Sb.

Reference may be made in this respect to WO 2007/079431 (on page 7, lines 1-5 and 28-32) and EP 939071 (paragraph [0022]), WO 2008/054781 (on page 9, line 22 to page 10, line 34) and WO 2008/040969 (claim 1), to which reference is expressly made.

The catalyst is more particularly preferably chromium-based and it is more particularly a mixed catalyst comprising chromium.

According to one embodiment, a mixed catalyst comprising chromium and nickel is used. The Cr/Ni mole ratio (on the basis of the metal element) is generally from 0.5 to 5, for example from 0.7 to 2, for example about 1. The catalyst may contain from 0.5% to 20% by weight of nickel.

The metal may be present in metallic form or in the form of a derivative, for example an oxide, halide or oxyhalide. These derivatives are preferably obtained by activation of the catalytic metal.

The support is preferably constituted with aluminum, for example alumina, activated alumina or aluminum derivatives, such as aluminum halides and aluminum oxyhalides, for example described in U.S. Pat. No. 4,902,838, or obtained via the activation process described above.

The catalyst may comprise chromium and nickel in an activated or unactivated form, on a support which has optionally been subjected to activation.

Reference may be made to WO 2009/118628 (especially on page 4, line 30 to page 7, line 16), to which reference is expressly made herein.

Another preferred embodiment is based on a mixed catalyst containing chromium and at least one element chosen from Mg and Zn. The atomic ratio of Mg or Zn/Cr is preferably from 0.01 to 5.

Before its use, the catalyst is preferably subjected to activation with air, oxygen or chlorine and/or with HF.

The catalyst is preferably subjected to activation with air or oxygen and HF at a temperature from 100 to 500° C., preferably from 250 to 500° C. and more particularly from 300 to 400° C. The activation time is preferably from 1 to 200 hours and more particularly from 1 to 50 hours.

This activation may be followed by a final fluorination activation step in the presence of an oxidizing agent, HF and organic compounds.

The HF/organic compounds mole ratio is preferably from 2 to 40 and the oxidizing agent/organic compounds mole ratio is preferably from 0.04 to 25. The temperature of the final activation is preferably from 300 to 400° C. and its duration is preferably from 6 to 100 hours.

The gas-phase fluorination reaction may be performed:
- with an HF/compound of formula (I) and/or (II) mole ratio from 3:1 to 150:1, preferably from 4:1 to 125:1 and more particularly preferably from 5:1 to 100:1;
- with a contact time from 3 to 100 seconds, preferably 4 to 75 seconds and more particularly 5 to 50 seconds (volume of catalyst divided by the total entering stream, adjusted to the operating temperature and pressure);
- at a pressure ranging from atmospheric pressure to 20 bar, preferably from 2 to 18 bar and more particularly from 3 to 15 bar;
- at a temperature (temperature of the catalytic bed) from 200 to 450° C., preferably from 250 to 400° C. and more particularly from 280 to 380° C.

The duration of the reaction step is typically from 10 to 8000 hours, preferably from 50 to 5000 hours and more particularly preferably from 70 to 1000 hours.

An oxidizing agent, preferably oxygen, may optionally be added during the fluorination reaction. The oxygen/organic compounds mole ratio may be from 0.005 to 2, preferably from 0.01 to 1.5. Oxygen may be introduced in pure form or in the form of air or an oxygen/nitrogen mixture. Oxygen may also be replaced with chlorine.

Method for Selecting the Organic Extracting Agent

The selection of the organic extracting agent is determined by using the Cosmo-RS model implemented in the COSMOTHERM software. For this selected binary couple, a separation factor is calculated for each of the solvents studied via the following equation:

$S_{1,2} = (\gamma_{1,S} * P1)/(\gamma_{2,S} * P2)$ in which $\gamma_{1,S}$ represents the activity coefficient of the first compound 1 in the organic extracting agent under consideration at infinite dilution, P1 represents the saturating vapor pressure of the first compound 1, $\gamma_{2,S}$ represents the activity coefficient of the second compound 2 of the binary couple in the organic extracting agent under consideration at infinite dilution, P2 represents the saturating vapor pressure of the second compound.

An absorption capacity is also calculated for each of the solvents studied and for a binary couple (1,2) under consideration. The absorption capacity is calculated via the formula $C_{2,S} = 1/(\gamma_{2,S})$ in which $\gamma_{2,S}$ represents the activity coefficient of the second compound of the binary couple under consideration in said organic extracting agent studied at infinite dilution. The calculations are repeated for each organic extracting agent studied. Minimum separation factor and absorption capacity values are identified so as to allow a sufficient separation between the first compound and the second compound of the binary couple (1,2) under consideration. The saturating vapor pressure is considered for a temperature of 25° C.

EXAMPLES

To purify 2,3,3,3-tetrafluoro-1-propene, the binary couple 2,3,3,3-tetrafluoro-1-propene/trans-1,3,3,3-tetrafluoro-1-propene (1234ze-E) is considered to select the organic extracting agent (see table 1). The mixture to be purified comprises 2,3,3,3-tetrafluoro-1-propene, 1,1,1,2,2-pentafluoropropane and trans-1,3,3,3-tetrafluoro-1-propene (1234ze-E).

TABLE 1 capacity and separation factor of the organic extracting agent

| Organic extracting agent | (1234zeE) absorption capacity | (1234yf/1234zeE) separation factor | (245cb/1234zeE) separation factor |
|---|---|---|---|
| Ethylamine | 1.95 | 2.92 | 3.60 |
| Isopropylamine | 1.85 | 2.56 | 3.14 |
| Diethyl ether | 1.48 | 1.79 | 1.68 |
| n-Propylamine | 1.86 | 2.61 | 3.14 |
| Diethylamine | 1.57 | 1.88 | 2.18 |
| Diethoxymethane | 1.41 | 1.86 | 1.63 |
| Isopropyl acetate | 1.42 | 2.15 | 1.79 |
| 3-Pentylamine | 1.63 | 2.05 | 2.39 |
| 2-Methoxyethanamine | 1.98 | 3.19 | 3.80 |
| tert-Butyl acetate | 1.37 | 2.10 | 1.63 |
| Dioxane | 1.09 | 2.24 | 1.92 |
| 1,1-Diethoxyethane | 1.54 | 1.90 | 1.78 |
| Trimethoxymethane | 1.28 | 2.11 | 1.81 |
| n-Pentylamine | 1.64 | 2.31 | 2.71 |
| 1,3-Dioxane | 1.09 | 2.23 | 1.93 |
| sec-Butyl acetate | 1.45 | 2.12 | 1.79 |
| 1,2-Diaminoethane | 1.29 | 4.43 | 6.88 |
| 1-Methoxy-2-propanol | 0.87 | 2.31 | 2.15 |
| 1,2-Propanediamine | 1.50 | 3.54 | 4.92 |
| n-Butyl acetate | 1.35 | 2.14 | 1.86 |
| 2-Methoxy-1-propanol | 0.87 | 2.31 | 2.13 |
| Hexanal | 1.09 | 1.98 | 1.72 |

The invention claimed is:

1. A process for purifying 2,3,3,3-tetrafluoro-1-propene (1234yf) using a first composition comprising 2,3,3,3-tetrafluoro-1-propene, 1,1,1,2,2-pentafluoropropane (245cb) and trans-1,3,3,3-tetrafluoro-1-propene (1234ze-E), said process comprising:
   a) placing said first composition in contact with at least one organic extracting agent to form a second composition;
   b) distilling said second composition by extractive distillation to form:
      i. a third composition comprising said organic extracting agent and trans-1,3,3,3-tetrafluoro-1-propene (1234ze-E); and
      ii. a stream comprising 2,3,3,3-tetrafluoro-1-propene (1234yf) and 1,1,1,2,2-pentafluoropropane (245cb); and
   c) recovering and separating said third composition to form a stream comprising said organic extracting agent and a stream comprising trans-1,3,3,3-tetrafluoro-1-propene (1234ze-E).

2. The process as claimed in claim 1, further comprising recovering said stream ii) comprising 2,3,3,3-tetrafluoro-1-propene and 1,1,1,2,2-pentafluoropropane (245cb) obtained in step b), and distilling said stream to form a stream A comprising 2,3,3,3-tetrafluoro-1-propene and a stream B comprising 1,1,1,2,2-pentafluoropropane (245cb).

3. The process as claimed in claim 1, wherein said first composition also comprises at least one of the compounds selected from the group consisting of chloromethane (40), 1,1-difluoroethane (152a), 1,1,1,2-tetrafluoroethane (134a), chloropentafluoroethane (115), trans-1,2,3,3,3-pentafluoropropene (1225ye-E), cis-1,2,3,3,3-pentafluoropropene (1225ye-Z) and 3,3,3-trifluoropropene (1243zf).

4. The process as claimed in claim 3, wherein said at least one of the compounds selected from the group consisting of chloromethane (40), 1,1-difluoroethane (152a), 1,1,1,2-tetrafluoroethane (134a), chloropentafluoroethane (115), trans-1,2,3,3,3-pentafluoropropene (1225ye-E), cis-1,2,3,3,3-pentafluoropropene (1225ye-Z) and 3,3,3-trifluoropropene (1243zf) is also contained in said second and third compositions; and step c) of the process comprises recovering and separating said third composition to form a stream comprising said organic extracting agent and another stream comprising trans-1,3,3,3-tetrafluoro-1-propene (1234ze-E) and said at least one of the compounds selected from the group consisting of chloromethane (40), 1,1-difluoroethane (152a), 1,1,1,2-tetrafluoroethane (134a), chloropentafluoroethane (115), trans-1,2,3,3,3-pentafluoropropene (1225ye-E), cis-1,2,3,3,3-pentafluoropropene (1225ye-Z) and 3,3,3-trifluoropropene (1243zf).

5. The process as claimed in claim 1, wherein said organic extracting agent comprises a solvent selected from the group consisting of halohydrocarbon, alcohol, ketone, amine, ester, ether, aldehyde, nitrile, carbonate, thioalkyl, amide and heterocycle; or the organic extracting agent comprises triethylfluorosilane.

6. The process as claimed in claim 1, wherein said organic extracting agent has a separation factor $S_{1,2}$ of greater than or equal to 1.1, said separation factor being calculated by the formula $S_{1,2}=(\gamma_{1,S}*P1)/(\gamma_{2,S}*P2)$ wherein
   $\gamma_{1,S}$ represents the activity coefficient of 2,3,3,3-tetrafluoro-1-propene in said organic extracting agent at infinite dilution;
   P1 represents the saturating vapor pressure of 2,3,3,3-tetrafluoro-1-propene;
   $\gamma_{2,S}$ represents the activity coefficient of trans-1,3,3,3-tetrafluoro-1-propene (1234ze-E) in said organic extracting agent at infinite dilution; and
   P2 represents the saturating vapor pressure of trans-1,3,3,3-tetrafluoro-1-propene (1234ze-E).

7. The process as claimed in claim 1, wherein said organic extracting agent has a separation factor $S_{1,2}$ of greater than or equal to 1.1, said separation factor being calculated by the formula $S_{1,2}=(\gamma_{1,S}*P1)/(\gamma_{2,S}*P2)$ wherein
   $\gamma_{1,S}$ represents the activity coefficient of 1,1,1,2,2-pentafluoropropane (245cb) in said organic extracting agent at infinite dilution;
   P1 represents the saturating vapor pressure of 1,1,1,2,2-pentafluoropropane (245cb);
   $\gamma_{2,S}$ represents the activity coefficient of trans-1,3,3,3-tetrafluoro-1-propene (1234ze-E) in said organic extracting agent at infinite dilution; and
   P2 represents the saturating vapor pressure of trans-1,3,3,3-tetrafluoro-1-propene (1234ze-E).

8. The process as claimed in claim 1, wherein said organic extracting agent has an absorption capacity $C_{2,S}$ of greater than or equal to 0.20, said absorption capacity being calculated by the formula $C_{2,S}=1/(\gamma_{2,S})$ wherein $\gamma_{2,S}$ represents the activity coefficient of said at least one compound consisting of trans-1,3,3,3-tetrafluoro-1-propene (1234ze-E) in said organic extracting agent at infinite dilution.

9. The process as claimed in claim 1, wherein said organic extracting agent is selected from the group consisting of ethylamine, isopropylamine, diethyl ether, n-propylamine, diethylamine, propanone, methyl acetate, butanone, diethoxymethane, isopropyl acetate, 3-pentylamine, 2-methoxyethanamine, tert-butyl acetate, dioxane, 1,1-diethoxyethane, trimethoxymethane, n-pentylamine, 1,3-dioxane, sec-butyl acetate, 1,2-diaminoethane, 1-methoxy-2-propanol, 1,2-propanediamine, n-butyl acetate, 2-methoxy-1-propanol and hexanal.

10. The process as claimed in claim 1, wherein the stream ii) comprising 2,3,3,3-tetrafluoro-1-propene and 1,1,1,2,2-pentafluoropropane (245cb) formed in step b) is recovered and is free of trans-1,3,3,3-tetrafluoro-1-propene (1234ze-E).

11. The process as claimed in claim 1, further comprising, prior to step a):
   i') using a composition comprising 2,3,3,3-tetrafluoro-1-propene, impurities with a boiling point below the boiling point of 2,3,3,3-tetrafluoro-1-propene, 1,1,1,2,2-pentafluoropropane (245cb), and trans-1,3,3,3-tetrafluoro-1-propene (1234ze-E), optionally at least one compound selected from the group consisting of chloromethane (40), 1,1-difluoroethane (152a), 1,1,1,2-tetrafluoroethane (134a), chloropentafluoroethane (115), trans-1,2,3,3,3-pentafluoropropene (1225ye-E), cis-1,2,3,3,3-pentafluoropropene (1225ye-Z), 3,3,3-trifluoropropene (1243zf), and optionally heavy impurities;
   ii') distilling said composition from step i) to remove, at the top of the column, impurities with a boiling point below the boiling point of 2,3,3,3-tetrafluoro-1-propene and to form a first stream comprising 2,3,3,3-tetrafluoro-1-propene, 1,1,1,2,2-pentafluoropropane (245cb) and trans-1,3,3,3-tetrafluoro-1-propene (1234ze-E), optionally at least one compound selected from the group consisting of chloromethane (40), 1,1-difluoroethane (152a), 1,1,1,2-tetrafluoroethane (134a), chloropentafluoroethane (115), trans-1,2,3,3,3-pentafluoropropene (1225ye-E), cis-1,2,3,3,3-pentafluoropropene (1225ye-Z), 3,3,3-trifluoropropene (1243zf), and optionally heavy impurities, recovered at the bottom of the distillation column; and
   iii') optionally, distilling said first stream recovered at the bottom of the distillation column in step ii') to recover, at the top of the column, a second stream comprising 2,3,3,3-tetrafluoro-1-propene, 1,1,1,2,2-pentafluoropropane (245cb) and trans-1,3,3,3-tetrafluoro-1-propene (1234ze-E), and optionally at least one compound selected from the group consisting of chloromethane (40), 1,1-difluoroethane (152a), 1,1,1,2-tetrafluoroethane (134a), chloropentafluoroethane (115), trans-1,2,3,3-pentafluoropropene (1225ye-E), cis-1,2,3,3,3-pentafluoropropene (1225ye-Z) and 3,3,3-trifluoropropene (1243zf), and, at the bottom of the distillation column, a stream comprising the heavy impurities;
wherein said first stream recovered in step ii') or said second stream recovered in step iii') corresponding to said first composition used in step a).

12. A process for producing and purifying 2,3,3,3-tetrafluoro-1-propene, comprising:
   A) fluorination in the presence of a catalyst for a compound of formula (I) $CX(Y)_2$—$CX(Y)_m$—$CH_mXY$ wherein X and Y independently represent a hydrogen, fluorine or chlorine atom and m =0 or 1; and/or catalytic fluorination in the presence of a catalyst for a compound of formula $(CX_nY_{3-n})CH_pX_{1-p}CH_mX_{2-m}$ (II) wherein X is, independently of each other, Cl, F, I or Br; Y is, independently of each other, H, Cl, F, I or Br; n is 1,2 or 3; and m is 0, 1 or 2; and p is 0 or 1;
   B) recovering a stream comprising 2,3,3,3-tetrafluoro-1-propene, 1,1,1,2,2-pentafluoropropane (245cb), and trans-1,3,3,3-tetrafluoro-1-propene (1234ze E); and
   C) purifying 2,3,3,3-tetrafluoro-1-propene as claimed in claim 1 using the stream recovered in step B).

13. A composition comprising 2,3,3,3-tetrafluoropropene, 1,1,1,2,2-pentafluoropropane (245cb), trans-1,3,3,3-tetrafluoro-1-propene (1234ze-E) and an organic extracting agent with a separation factor $S_{1,2}$ of greater than or equal to 1.60, said separation factor being calculated by the formula $S_{1,2}=$ $(\gamma_{1,S}*P1)/(\gamma_{2,S}*P2)$ wherein $\gamma_{1,S}$ represents the activity coefficient of 2,3,3,3-tetrafluoropropene in said organic extracting agent at infinite dilution, P1 represents the saturating vapor pressure of 2,3,3,3-tetrafluoropropene, $\gamma_{2,S}$ represents the activity coefficient of trans-1,3,3,3-tetrafluoro-1-propene (1234ze-E) in said organic extracting agent at infinite dilution, and P2 represents the saturating vapor pressure of trans-1,3,3,3-tetrafluoro-1-propene (1234ze-E), wherein the composition is free of HF.

14. The composition as claimed in claim 13, wherein the organic extracting agent is selected from the group consisting of ethylamine, isopropylamine, diethyl ether, n-propylamine, diethylamine, propanone, methyl acetate, butanone, diethoxymethane, isopropyl acetate, 3-pentylamine, 2-methoxyethanamine, tert-butyl acetate, dioxane, 1,1-diethoxyethane, trimethoxymethane, n-pentylamine, 1,3-dioxane, sec-butyl acetate, 1,2-diaminoethane, 1-methoxy-2-propanol, 1,2-propanediamine, n-butyl acetate, 2-methoxy-1-propanol and hexanal.

* * * * *